United States Patent [19]

Morimoto et al.

[11] Patent Number: 5,284,661
[45] Date of Patent: Feb. 8, 1994

[54] FUSED THIOPHENE DERIVATIVES, THEIR PRODUCTION AND USE

[75] Inventors: Akira Morimoto, Osaka; Kohei Nishikawa, Kyoto; Takehiko Naka, Hyogo, all of Japan

[73] Assignee: Takeda Chemical Industries, Ltd., Osaka, Japan

[21] Appl. No.: 47,368

[22] Filed: Apr. 19, 1993

Related U.S. Application Data

[63] Continuation of Ser. No. 657,051, Feb. 19, 1991, abandoned.

[30] Foreign Application Priority Data

Feb. 22, 1990 [JP] Japan .................................. 2-42125
Jan. 17, 1991 [JP] Japan .................................. 3-3958

[51] Int. Cl.$^5$ .................... A61K 9/20; C07D 495/04
[52] U.S. Cl. .................... 424/464; 514/233.8; 514/253; 514/301; 514/321; 514/258; 544/127; 544/362; 544/278; 546/114; 546/198
[58] Field of Search .............. 424/464; 546/114, 198; 544/127, 362; 514/233.8, 253, 301, 321

[56] References Cited

U.S. PATENT DOCUMENTS

| | | | |
|---|---|---|---|
| 4,670,560 | 6/1987 | Press | 544/278 |
| 4,835,157 | 5/1989 | Press | 514/258 |
| 4,880,804 | 11/1989 | Carini et al. | 514/234.5 |

FOREIGN PATENT DOCUMENTS

| | | |
|---|---|---|
| 0288834 | 5/1981 | European Pat. Off. |
| 0245637 | 11/1987 | European Pat. Off. |
| 0253310 | 1/1988 | European Pat. Off. |
| 0291969 | 11/1988 | European Pat. Off. |
| 0323841 | 7/1989 | European Pat. Off. |
| 0400835 | 5/1990 | European Pat. Off. |

OTHER PUBLICATIONS

CA 89:129437q (1978) Synthesis and antibacterial evaluation of 4,7-dihydro-4-oxothieno[2,3-b]-pyridine-5-carboxylic acids by Gilis et al.
Ronald K. Russell et al., "Thiophene Systems. 9. Thienopyrimidinedione Derivatives as Potential Antihypertensive Agents", *J. Med. Chem.* 1988, vol. 31, pp. 1786-1793.
*Chemical Abstracts*, 99(3): 22419q (Jul. 19, 1983), p. 616, Colombus, Ohio.
Pancras C. Wong et al., "Nonpeptide Angiotensin II Receptor Antagonists. IV. EXP6155 and EXP6803" *Hypertension*, vol. 13 (1989), pp. 489-497, Dallas, Texas.
Pancras C. Wong et al., "Nonpeptide Angiotensin II Receptor Anatgonists. I. Pharmacological Characterization of 2-n-Butyl-4-chloro- . . . ", *J. Pharm. and Exper. Therapeutics*, vol. 247, No. 1 (Oct. 1988) pp. 1-7.

*Primary Examiner*—Thurman K. Page
*Assistant Examiner*—Jyothsna Venkat
*Attorney, Agent, or Firm*—Wegner, Cantor, Mueller & Player

[57] ABSTRACT

Novel fused thiophene derivatives of the formula (I):

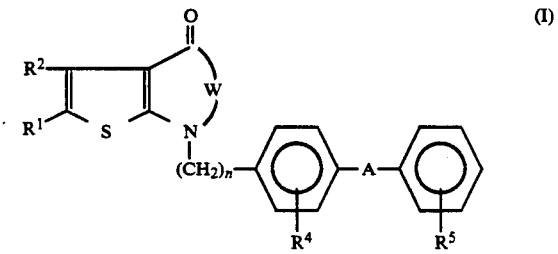

wherein W is

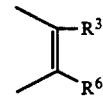

$R^1$ and $R^2$ which may be same or different, are each independently hydrogen, halogen, cyano, nitro, acylamino, or a hydrocarbon residue which may be substituted; $R^3$ is hydrogen, optionally substituted alkyl or alkenyl, or —COD wherein D is hydrogen, alkoxy, hydroxy, halogen, or optionally substituted amino; $R^4$ is hydrogen, halogen or nitro; $R^5$ is a residue capable of forming an anion or a residue convertible into an anion; $R^6$ is hydrogen or optionally substituted alkyl or alkenyl; A is a direct bond or a spacer having atomic length of two or less between the phenylene group and the phenyl group; and n is an integer of 1 or 2; and the pharmaceutically acceptable salts thereof have potent angiotensin II antagonist activity and antihypertensive activity, thus being useful as therapeutic agents for treating circulatory system diseases such as hypertensive diseases, heart diseases, strokes, etc.

13 Claims, No Drawings

FUSED THIOPHENE DERIVATIVES, THEIR PRODUCTION AND USE

This application is a continuation of U.S. application Ser. No. 07/657,051 filed Feb. 19, 1991, now abandoned.

FIELD OF THE INVENTION

The present invention relates to novel fused thiophene derivatives having potent pharmacological activity and antermediates for the preparation thereof. More particularly, the present invention relates to compounds having potent angiotensin II antagonist activity and antihypertensive activity, which are useful as therapeutic agents for treating circulatory diseases such as hypertensive diseases, heart diseases, strokes, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensin II converting enzyme inhibitors (ACE inhibitor) (this converting enzyme produces angiotensin II which possesses strong vasoconstrictive activity) has clarified the relation between the renin-angiotensin system and hypertension. Since angiotensin II elevates blood pressure via the angiotensin II receptors on cell membranes, angiotensin II antagonists as well as the ACE inhibitor would be useful in treating hypertension.

It has been reported that various angiotensin II analogues such as saralasin, [Sar$^1$,Ile$^8$]A II, and the like, possess potent angiotensin II antagonist activity.

It has, however, been reported that, when peptide antagonists are administered parenterally, their actions are not prolonged and, when administered orally, they are ineffective (M. A. Ondetti and D. W. Cushman, Annual Reports in Medicinal Chemistry, 13, 82-91 (1978)).

Non-peptide angiotensin II antagonists are disclosed in Japanese Patent Laid Open No. 71073/1981; No. 71074/1981; No. 92270/1982; No. 157768/1983; No. 240683/1987; No. 23868/1988; and No. 117876/1989, and European Patent Laid Open No. 0323841, etc.

Imidazole derivatives having angiotensin II antagonist activity are disclosed in A. T. Chiu et al., Eur. J. Pharm., 157, 13 (1981), P. C. Wong et al., J. Pharmcol. Exp. Ther., 247, 1 (1988), P. C. Wong et al., Hypertension, 13, 489 (1989), etc.

It has not yet been known that fused thiophene derivatives possess potent angiotensin II antagonist activity.

SUMMARY OF THE INVENTION

The present inventors made extensive investigations to prepare useful compounds which have angiotensin II antagonist activity. As a result of these researches, the present inventors have succeeded in synthesizing fused thiophene derivatives possessing excellently potent angiotensin II antagonist activity and developed their work to accomplish the present invention.

The present invention provides fused thiophene derivatives having the formula I:

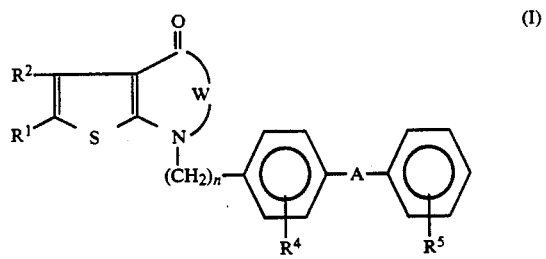

wherein W is

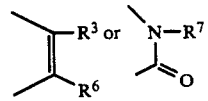

R$^1$ and R$^2$ which may be same or different, are each independently hydrogen, halogen, cyano, nitro, acylamino, or a hydrocarbon residue which may be substituted;

R$^3$ is hydrogen, optionally substituted alkyl or alkenyl, or —COD wherein D is hydrogen, alkoxy, hydroxy, halogen, or optionally substituted amino;

R$^4$ is hydrogen, halogen or nitro;

R$^5$ is a residue capable of forming an anion or a residue convertible into an anion;

R$^6$ is hydrogen or optionally substituted alkyl or alkenyl;

R$^7$ is a hydrocarbon residue which may be substituted;

A is a direct bond or a spacer having atomic length of two or less between the phenylene group and the phenyl group; and n is an integer of 1 or 2;

and the pharmaceutically acceptable salts thereof.

These compounds are potent angiotensin II antagonists which are of value in the treatment of circulatory system diseases such as hypertensive diseases, heart diseases, strokes, etc.

Another aspect of the present invention relates to pharmaceutical compositions comprising an effective amount of the fused thiophene derivative having the formula I and a pharmaceutically acceptable carrier useful in treating circulatory system diseases such as hypertensive diseases, heart diseases, strokes, etc., and processes for preparing such compounds and compositions.

Still another aspect of the present invention relates to a method for treating said circulatory system diseases of hosts, which comprises administering an effective amount of the fused thiophene derivative having the formula I or the pharmaceutical composition thereof to said host.

DETAILED DESCRIPTION OF THE INVENTION

The present invention provides fused thiophene derivatives having the formula I and the pharmaceutically acceptable salts thereof, which possess potent angiotensin II antagonist activity and are of value in the treatment of circulatory diseases such as hypertensive diseases, heart diseases, strokes, etc., pharmaceutical compositions comprising an effective amount of the fused thiophene derivative having the formula I and a pharmaceutically acceptable carrier useful in treating said circulatory diseases and processes for preparing such compounds and compositions.

The present invention further provides a method for treating said circulatory system diseases of hosts, which comprises administering an effective amount of the fused thiophene derivative having the formula I or the pharmaceutical composition thereof to said host.

An important group of compounds according to the present invention are the compounds of the formula Ia:

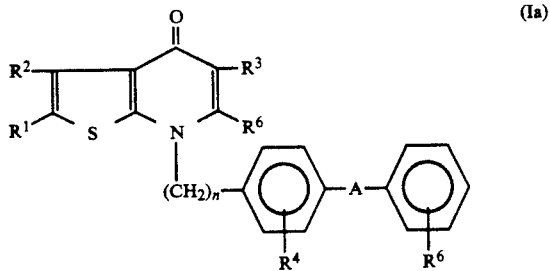

wherein $R^1$ and $R^2$ which may be same or different, are each independently hydrogen, halogen, cyano, nitro, acylamino, or a hydrocarbon residue which may be substituted;

$R^3$ is hydrogen, optionally substituted alkyl or alkenyl, or —COD wherein D is hydrogen, alkoxy, hydroxy, halogen, or optionally substituted amino;

$R^4$ is hydrogen, halogen or nitro;

$R^5$ is a residue capable of forming an anion or a residue convertible into an anion;

$R^6$ is hydrogen or optionally substituted alkyl or alkenyl;

A is a direct bond or a spacer having atomic length of two or less between the phenylene group and the phenyl group; and n is an integer of 1 or 2;

and the pharmaceutically acceptable salts thereof.

Another important group of compounds according to the present invention are the compounds of the formula Ib:

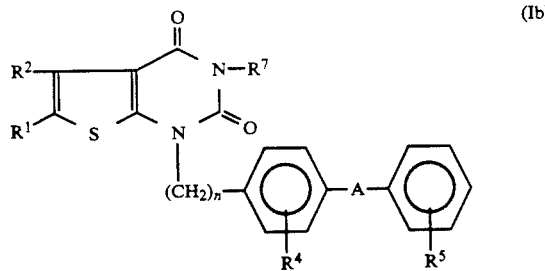

wherein $R^1$ and $R^2$ which may be same or different, are each independently hydrogen, halogen, cyano, nitro, acylamino, or a hydrocarbon residue which may be substituted;

$R^4$ is hydrogen, halogen or nitro;

$R^5$ is a residue capable of forming an anion or a residue convertible into an anion;

$R^7$ is a hydrocarbon residue which may be substituted;

A is a direct bond or a spacer having atomic length of two or less between the phenylene group and the phenyl group; and n is an integer of 1 or 2;

and the pharmaceutically acceptable salts thereof.

With regard to the foregoing formula (I), halogen for $R^1$ and $R^2$ include fluorine, chlorine, bromine, and iodine.

The acylamino groups for $R^1$ and $R^2$ include a group having the formula: $R^8CONH-$ wherein $R^8$ is hydrogen or a hydrocarbon residue which may be substituted.

Examples of hydrocarbon residues for $R^8$ include acyclic hydrocarbon residues such as lower alkyl of 1 to about 8 carbon atoms (e.g. methyl, ethyl, propyl, isopropyl, butyl, isobutyl, sec-butyl, t-butyl, pentyl, i-pentyl, hexyl, heptyl, octyl, and the like), lower alkenyl of 2 to about 8 carbon atoms (e.g. vinyl, allyl, isopropenyl, 2-butenyl, 2-pentenyl, 2-hexenyl, 2-octenyl, and the like), and lower alkynyl of 2 to about 8 carbon atoms (e.g. ethynyl, 2-butynyl, 2-pentynyl, 2-octynyl, and the like); cyclic hydrocarbon residues such as alicyclic hydrocarbon residues of 3 to about 8 carbon atoms (e.g. cyclopropyl, cyclopentyl, cyclohexyl, 2-cyclohexen-1-yl, cyclooctyl and the like), aromatic hydrocarbon residues of about 6 to 12 carbon atoms (e.g. phenyl, naphthyl and the like); etc.

Examples of hydrocarbon residues for $R^1$, $R^2$ and $R^7$ include acyclic hydrocarbon residues such as lower alkyl of 1 to about 8 carbon atoms (e.g. methyl, ethyl, propyl, isopropyl, butyl, isobutyl, sec-butyl, t-butyl, pentyl, i-pentyl, hexyl, heptyl, octyl, and the like), lower alkenyl of 2 to about 8 carbon atoms (e.g. vinyl, allyl, isopropenyl, 2-butenyl, 2-pentenyl, 2-hexenyl, 2-octenyl, and the like), and lower alkynyl of 2 to about 8 carbon atoms (e.g. ethynyl, 2-butynyl, 2-pentynyl, 2-octynyl, and the like); cyclic hydrocarbon residues such as alicyclic hydrocarbon residues of 3 to about 8 carbon atoms (e.g. cyclopropyl, cyclopentyl, cyclohexyl, 2-cyclohexen-1-yl, cyclooctyl and the like), aromatic hydrocarbon residues of about 6 to 12 carbon atoms (e.g. phenyl, naphthyl and the like); etc.

Said hydrocarbon residues for $R^1$, $R^2$ and $R^7$ may be optionally substituted with hydroxyl, lower ($C_{1-4}$) alkoxy (e.g. methoxy, ethoxy, and the like), lower ($C_{1-4}$) alkyl (e.g. methyl, ethyl, and the like), halogen (e.g. F, Cl, Br and the like), nitro, optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), N-arylamino (e.g. phenylamino, naphthylamino, etc.), N-aralkylamino (e.g. benzylamino, naphthylmethylamino, etc.) and alicyclic amino (e.g. morpholino, piperidino, piperazino, piperidylmethyl, N-phenylpiperazino, N-(p-fluorophenyl)piperazino, N-(m-methoxyphenyl)piperazino, etc.), acyloxy such as lower ($C_{1-4}$) alkanoyloxy (e.g. acetyloxy, etc.) and aroyloxy (e.g. benzoyloxy, etc.), aryl such as phenyl and naphthyl (e.g. phenyl which may be optionally substituted with halogen, nitro, lower ($C_{1-4}$) alkoxy, lower ($C_{1-4}$) alkyl or the like at an optional position on the phenyl ring), or a group having the formula: —COD' wherein D' is hydroxy, lower ($C_{1-4}$) alkoxy (e.g. methoxy, ethoxy, and the like), or optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), N-arylamino (e.g. phenylamino, naphthylamino, etc.), N-aralkylamino (e.g. benzylamino, naphthylmethylamino, etc.) and alicyclic amino (e.g. morpholino, piperidino, piperazino, N-phenylpiperazino, etc.). Said hydrocarbon residues for $R^1$ and $R^2$ may also be optionally taken together to form a ring.

Alkyl or alkenyl groups for $R^3$ and $R^6$ are lower alkyl of 1 to about 8 carbon atoms and lower alkenyl of 2 to about 8 carbon atoms which may be straight or branched. Examples of such alkyl and alkenyl groups for $R^3$ and $R^6$ include methyl, ethyl, propyl, isopropyl, butyl, isobutyl, sec-butyl, vinyl, allyl, isopropenyl, 2-butenyl, 2-pentenyl, 2-hexenyl, 2-octenyl, and the like. Said alkyl or alkenyl groups for $R^3$ and $R^6$ may be optionally substituted with hydroxyl, optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), halogen, lower ($C_{1-4}$) alkoxy (e.g. methoxyl, ethoxyl, and the like) and —COD″ wherein D″ is lower ($C_{1-4}$) alkoxy (e.g. methoxy, ethoxy, and the like), hydroxy, halogen, or optionally substituted amino as defined above (e.g. amino, N-lower ($C_{1-4}$) alkyl amino such as methylamino and ethylamino, N,N-dilower ($C_{1-4}$) alkyl amino such as dimethylamino and diethylamino, N-arylamino such as phenylamino and naphthylamino, N-aralkylamino such as benzylamino and naphthylmethylamino, alicyclic amino such as morpholino, piperidino, piperazino and N-phenylpiperazino, etc).

Where $R^3$ is a group having the formula: —COD, alkoxy groups for D include lower ($C_{1-4}$) alkoxy (e.g. methoxy, ethoxy, and the like). For D, examples of halogen include Cl, Br and the like, examples of optionally substituted amino include amino, N-lower ($C_{1-4}$) alkyl amino (e.g. methylamino, and the like), N,N-dilower ($C_{1-4}$) alkyl amino (e.g. dimethylamino, and the like), N-arylamino (e.g. phenylamino, and the like), N-aralkylamino (e.g. benzylamino, naphthylmethylamino, and the like), N-heteroarylamino (e.g. pyridylamino, and the like), N-heteroaralkylamino (e.g. pyridylmethylamino, and the like), alicyclic amino (e.g. morpholino, piperidino, piperazino, piperidylmethyl, N-phenyl-piperazino, N-(p-fluorophenyl)piperazino, and the like), wherein said alkyl, aryl and heteroaryl groups may be optionally substituted with alkyl (e.g. methyl, ethyl, propyl, isopropyl, butyl, isobutyl, sec-butyl, and the like), hydroxyl, optionally substituted amino (e.g. amino, N-lower ($C_{1-4}$) alkyl amino (e.g. methylamino, ethylamino, and the like), N,N-dilower ($C_{1-4}$) alkyl amino (e.g. dimethylamino, and the like), alicyclic amino (e.g. morpholino, piperidino, piperazino, N-phenylpiperazino, and the like)), halogen, nitro, lower ($C_{1-4}$) alkoxy (e.g. methoxyl, ethoxyl), or the like. The compounds wherein D is halogen are useful as synthetic intermediates for the preparation of those wherein D is alkoxy.

$R^4$ represents hydrogen, halogen (e.g. chlorine, bromine, and the like) or nitro, which may be in the ortho or meta position to the —A— group.

Examples of residues capable of forming an anion and residues convertible into the anion for $R^5$ include carboxyl, lower ($C_{1-4}$) alkoxycarbonyl, cyano, tetrazolyl, trifluoromethanesulfonic amide (—$NHSO_2CF_3$), phosphoric acid, sulfonic acid, and the like. Such residues may include those which are capable of forming anions either chemically or under biological and/or physiological conditions. $R^5$ is preferable in the ortho position. The compounds wherein $R^5$ is a residue capable of forming an anion or convertible thereinto chemically (e.g. by oxidation, reduction or hydrolysis) (e.g. cyano and the like), are useful as synthetic intermediates.

A shows that the adjacent phenylene group is bonded to the phenyl group directly or through a spacer whose atomic chain is 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene, —C(=O)—, —O—, —S—, —NH—, —C(=O)—NH—, O—$CH_2$—, —S—$CH_2$—, —CH=CH—, etc.

A preferred embodiment of the invention is a compound of the formula (Ia'):

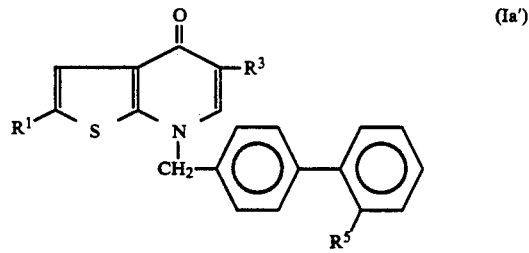

wherein $R^1$ is lower ($C_{1-8}$) alkyl; $R^3$ is hydrogen, optionally substituted lower ($C_{1-8}$) alkyl (e.g. lower ($C_{1-4}$) carbalkoxyvinyl, lower ($C_{1-4}$) alkoxylmethyl, and the like) or COD wherein D is hydrogen, lower ($C_{1-4}$) alkoxy, hydroxy, or optionally substituted amino (e.g. amino, N-lower ($C_{1-4}$) alkylamino, N,N-dilower ($C_{1-4}$) alkyl amino, phenylamino, methoxybenzylamino, halogenobenzylamino, pyridylmethylamino, piperidylmethylamino, pyridylpiperazinoalkylamino, piperidinoalkylamino, optionally substituted arylpiperazinoalkylamino and the like); and $R^5$ is carboxyl or tetrazolyl (inter alia tetrazolyl); and the pharmaceutically acceptable salts thereof.

A further preferred embodiment of the invention is a compound of the formula (Ib'):

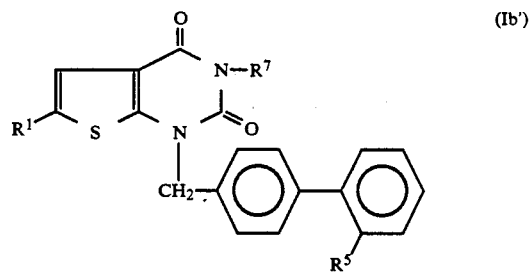

wherein $R^1$ is lower ($C_{1-8}$) alkyl; $R^7$ is hydrogen, lower ($C_{1-8}$) alkyl which may be optionally substituted with optionally substituted aryl, optionally substituted amino (e.g. amino, N-lower ($C_{1-4}$) alkyl amino, N,N-dilower ($C_{1-4}$) alkyl amino, phenylamino, benzylamino, morpholino, piperidino, piperazino, N-phenylpiperazino, and the like) or COD wherein D is lower ($C_{1-4}$) alkoxy, hydroxy, or optionally substituted amino (e.g. amino, N-lower ($C_{1-4}$) alkyl amino, N,N-dilower ($C_{1-4}$) alkyl amino, phenylamino, benzylamino, and the like), ($C_{3-8}$) cycloalkyl or optionally substituted aryl (e.g. halogenophenyl); and $R^5$ is carboxyl or tetrazolyl (inter alia tetrazolyl); and the pharmaceutically acceptable salts thereof.

The compounds (I) of the present invention may be prepared by several reaction schemes, as illustrated below for a preferred compound.

Scheme A

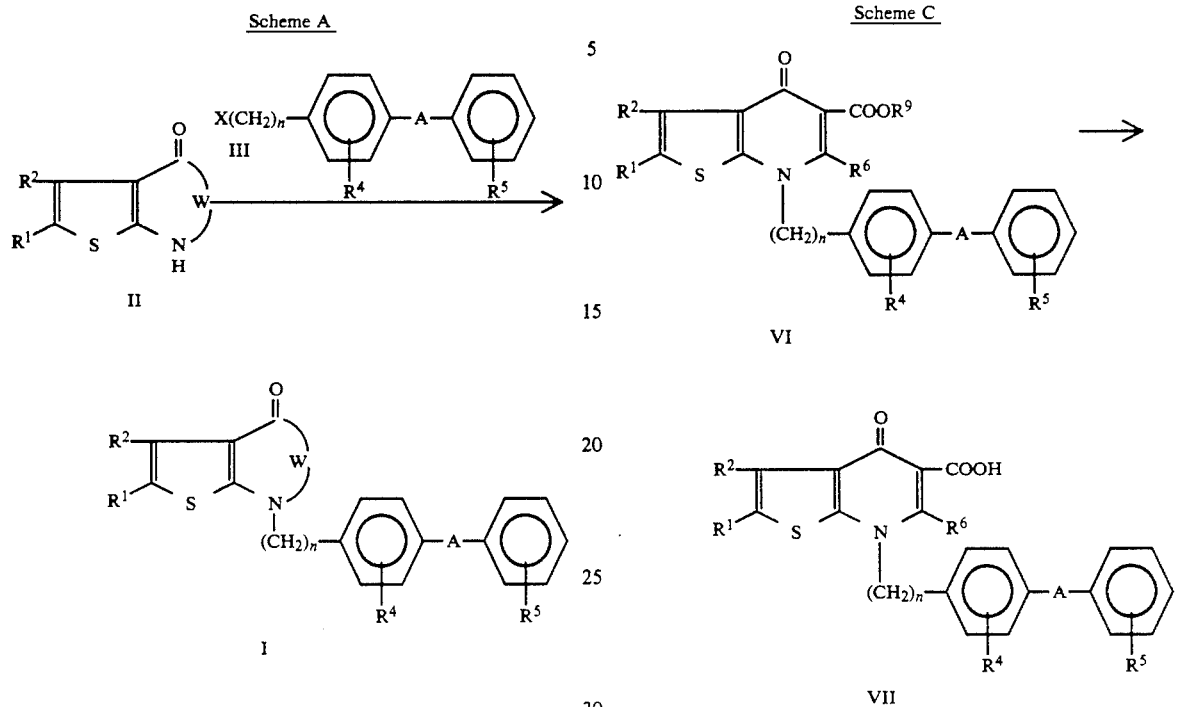

wherein $R^1$, $R^2$, $R^4$, $R^5$, A, W and n have the above-defined meanings, and X is halogen.

Scheme B wherein each group is of the same meaning as defined above.

Scheme C

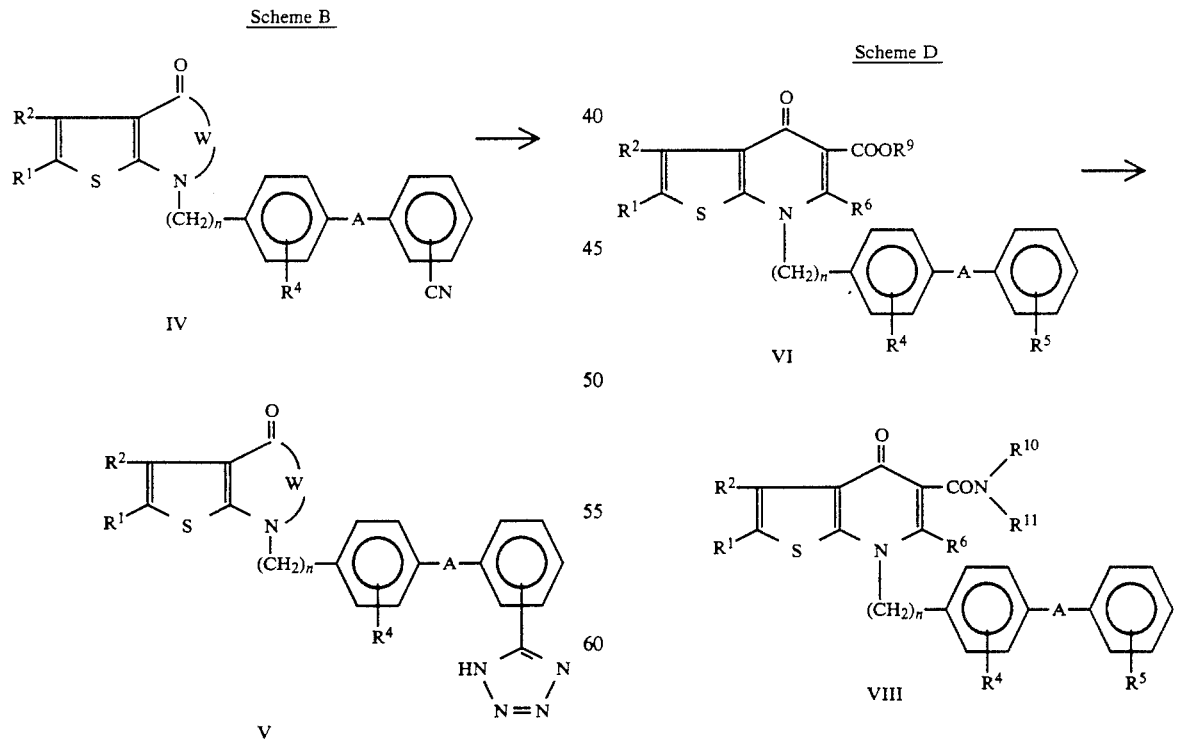

wherein $R^1$, $R^2$, $R^4$, $R^5$, $R^6$, A and n have the above-defined meanings, and $R^9$ is lower ($C_{1-4}$) alkyl.

Scheme D wherein $R^1$, $R^2$, $R^4$, $R^5$, $R^6$, $R^9$, A and n have the above-defined meanings, and $R^{10}$ and $R^{11}$ are each independently hydrogen or a hydrocarbon residue.

Scheme E

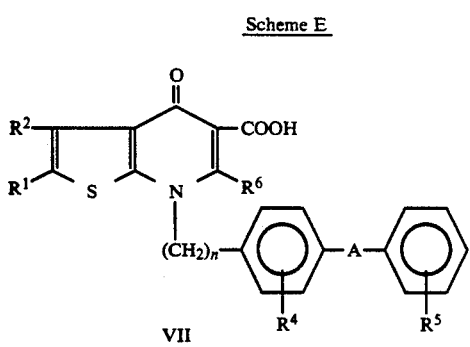

VII

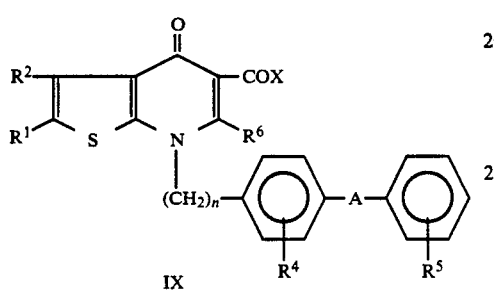

IX wherein $R^1$, $R^2$, $R^4$, $R^5$, $R^6$, A and n have the above-defined meanings, and X is halogen.

Scheme F

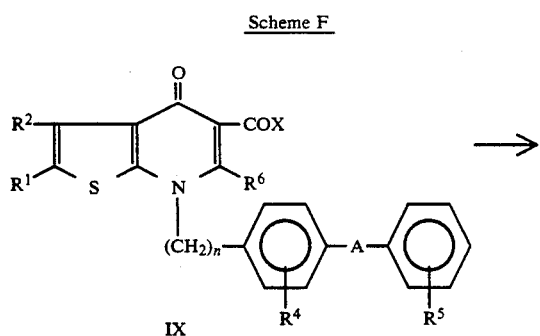

IX

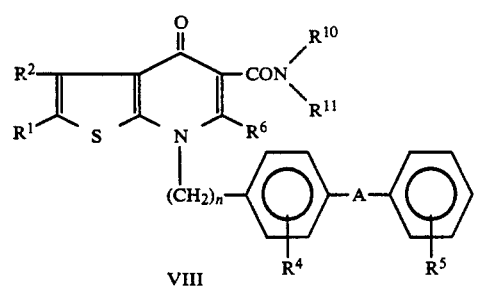

VIII wherein $R^1$, $R^2$, $R^4$, $R^5$, $R^6$, $R^{10}$, $R^{11}$, X, A and n have the above-defined meanings.

Scheme G

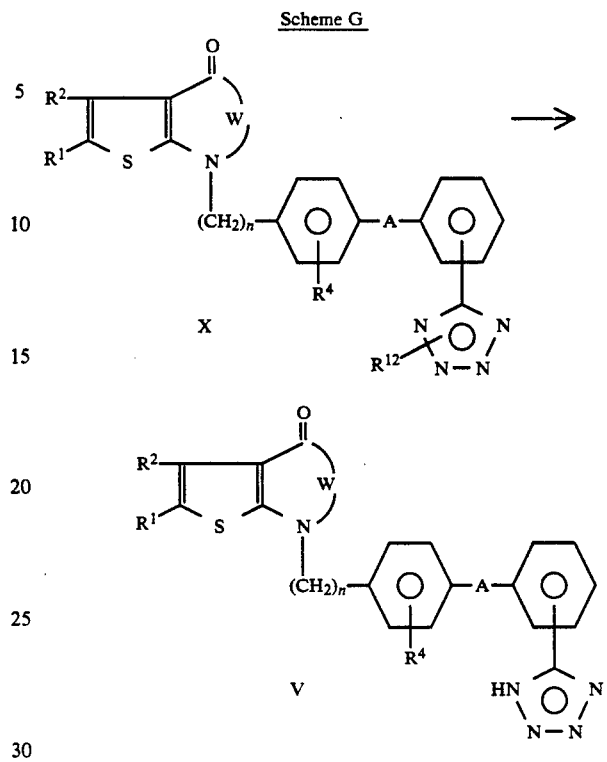

X

V wherein $R^1$, $R^2$, $R^4$, A, W and n have the above-defined meanings and $R^{12}$ is a protective group.

The reaction as illustrated in Scheme A is an alkylation using an alkylating agent in the presence of a base. One molar portion of the compound (II) is employed with 1 to 3 moles of the base and about 1 to about 3 moles of the alkylating agent. The reaction is conventionally conducted in solvents such as dimethylformamide, dimethylacetamide, dimethylsulfoxide, acetonitrile, acetone, ethylmethylketone, and the like. Examples of such bases include sodium hydride, potassium t-butoxide, cesium carbonate, potassium carbonate, sodium carbonate, and the like. Examples of such alkylating agents include substituted halides (e.g. chlorides, bromides, iodides, and the like), substituted sulfonate esters (e.g. methyl p-toluenesulfonate esters, and the like), etc.

The reaction conditions may vary depending on the combination of the base and the alkylating agent. A temperature in the range of from ice-cooling to 100° C. is preferred and a reaction period of from about 1 to about 10 hours is preferably employed.

The cyano substituent on the benzene of the compounds (IV) is reacted with various azides to form the tetrazole compounds (V) as illustrated in Scheme B. One molar portion of the compound (IV) is employed with about 1 to about 10 moles of the azide. The reaction is conventionally conducted in solvents such as dimethyl-formamide, diemthylacetamide, toluene, benzene, and the like.

Examples of such azides include trialkyl-tin azide, triphenyl-tin azide, hydrogen azide, and the like. In the case where the organo-tin azide compound is employed, the reaction is carried out in toluene or benzene by heating under reflux for a period of from about 10 to about 30 hours. When the hydrogen azide is used, 5 moles of sodium azide and ammonium chloride per compound (IV) are employed and the reaction is conducted in dimethylformamide at a temperature ranging from about 100° C. to about 130° C. for 1 to 10 days. During this reaction, it is preferable to facilitate working by adding an appropriate amount of sodium azide and ammonium chloride.

The reaction as illustrated in Scheme C is hydrolysis of the ester (VI) into the carboxylic acid (VII) in the presence of an alkali. One molar portion of the compound (VI) is employed with 1 to 3 moles of the alkali. The reaction is conventionally conducted in solvents such as alcohols containing water (e.g. methanol, ethanol, methylcellosolve, and the like). Examples of such alkalis include sodium hydroxide, potassium hydroxide, and the like. The reaction is preferably conducted at a temperature in the range from room temperature to 100° C. for a period from about 1 to about 10 hours.

The compounds (VI) are reacted with various amines to form the amide compounds (VIII) as illustrated in Scheme D. One molar portion of the compound (VI) is employed with about 2 to 50 moles of the amine. The reaction is conventionally conducted in solvents such as alcohols (e.g. methanol, ethanol, and the like) or without a solvent. The reaction is preferably conducted at a temperature in the range from room temperature to 200° C. Examples of such amines include ammonia, alkylamines (e.g. methylamine, ethylamine, propylamine, dimethylamine, diethylamine, butylamine, hydroxyethylamine, etc.), aralkylamines (e.g. benzylamine, phenetylamine, N-benzyl-N-methylamine, o-methoxybenzylamine, etc.), arylamines (e.g. aniline, N-methylaniline, etc.), heteroaralkylamines (e.g. 2-, 3- or 4-pyridylmethylamine, etc.), alicyclic amines (e.g. morpholine, piperidine, piperazine, N-phenylpiperazine, 2-piperidylmethylamine, 3-(p-fluorophenyl-piperazino)-propylamine, etc.), and the like.

The compounds (VII) are treated with various halogenating agents to form the acid halides (IX) as illustrated in Scheme E. One molar portion of the compound (VII) is employed with about 1 to 5 moles of the halogenating agent. The reaction is conventionally conducted in solvents such as halogenated hydrocarbons (e.g. $CHCl_3$, $CH_2Cl_2$, $ClCH_2CH_2Cl$, and the like), ethers (e.g. tetrahydrofuran, dioxane, and the like) and aromatic hydrocarbons (e.g. benzene, toluene, and the like). Examples of such halogenating agents include oxalyl chloride, thionyl chloride, phosphorous oxychloride, phosphorous trichloride, phosphorous pentachloride, etc. The reaction is preferably conducted at a temperature in the range from room temperature to 100° C. for a period from about 1 to about 10 hours.

The acid halides (IX) are reacted with various amines to form the amide compounds (VIII) as illustrated in Scheme F. One molar portion of the compound (IX) is employed with about 2 to 50 moles of the amine. The reaction is conventionally conducted in solvents such as alcohols (e.g. methanol, ethanol, and the like) and ethers (e.g. ethyl ether, tetrahydrofuran, dioxane, and the like). Examples of such amines include ammonia, alkylamines (e.g. methylamine, ethylamine, propylamine, dimethylamine, diethylamine, butylamine, hydroxyethylamine, etc.), aralkylamines (e.g. benzylamine, phenetylamine, N-benzyl-N-methylamine, o-methoxybenzylamine, etc.), arylamines (e.g. aniline, N-methylaniline, etc.), heteroaralkylamines (e.g. 2-, 3- or 4-pyridylmethylamine, etc.), alicyclic amines (e.g. morpholine, piperidine, piperazine, N-phenylpiperazine, 2-piperidylmethylamine, 3-(p-fluorophenylpiperazino)propylamine, etc.), and the like.

The protective group ($R^{12}$) on the tetrazole compound (X) leaves to form the tetrazole compound (V) as illustrated in Scheme G. Reaction conditions may vary depending on the protective group ($R^{12}$) used. When $R^{12}$ is triphenylmethyl (trityl), 2-tetrahydropyranyl, methoxymethyl, ethoxymethyl, or the like, the leaving of the protective group is conveniently conducted in aqueous alcohols (e.g. methanol, ethanol, etc) containing from about 0.5N to about 2N hydrochloric acid or acetic acid, or in a mixture of trifluoroacetic acid and water (1:2~5) at room temperature for a period from about 1 to about 10 hours.

The compounds (I) thus produced via the reaction processes as depicted in Schemes A, B, C, D, E, F and G can be isolated and purified from the reaction mixture according to conventional methods such as, for example, evaporation of solvents, extraction by water or organic solvents, concentration, neutralization, recrystallization, distillation, column chromatography and the like, to obtain a crystalline or oily product.

The compounds (I) of the present invention can be used in the form of salts derived from pharmaceutically or physiologically acceptable acids or bases. These salts include but are not limited to the following: salts with inorganic acids such as hydrochloric acid, sulphuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases.

The starting materials (II) can be easily prepared by or according to the known techniques, for example, as disclosed in:

(1) P. Blaszkiewicz, H. Vorbruggen and H. J. Kesler (Schering AG): DOS 2, 447,477 (15. 4. 76); Chem. Abst., 85, 46627 (1976), (2) Y. Kuwada, K. Meguro, Y. Sato and T. Fugono (Takeda Chem.): DOS 2, 435,025 (6. 25. 75); Chem. Abst., 82, 156252 (1975), etc.

Among the starting materials (III), the compounds wherein n is 1 (the compounds (IIIa)) is prepared by the known techniques as disclosed in Japanese Patent Laid Open No. 23868/1988; and No. 117876/1989, and European Patent Laid Open No. 0323841.

As illustrated in Scheme H, the compounds (IIIa) can also be easily prepared by halogenomethylation of the compounds (X) commercially available or easily prepared according to methods described in known literatures such as, for example, A. A. Vansheidt et al., Khim. Nauka i Prom., 2, 799 (1957).

Scheme H

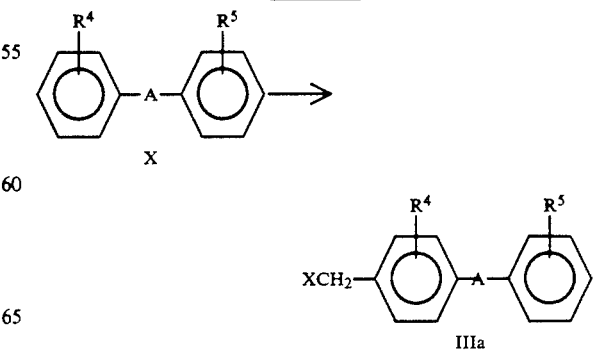

wherein each group has the above-defined meaning.

The compound (III) wherein n is 2 (the compounds (IIIb)) can be prepared from the compounds (IIIa) according to the methods as illustrated in Scheme I.

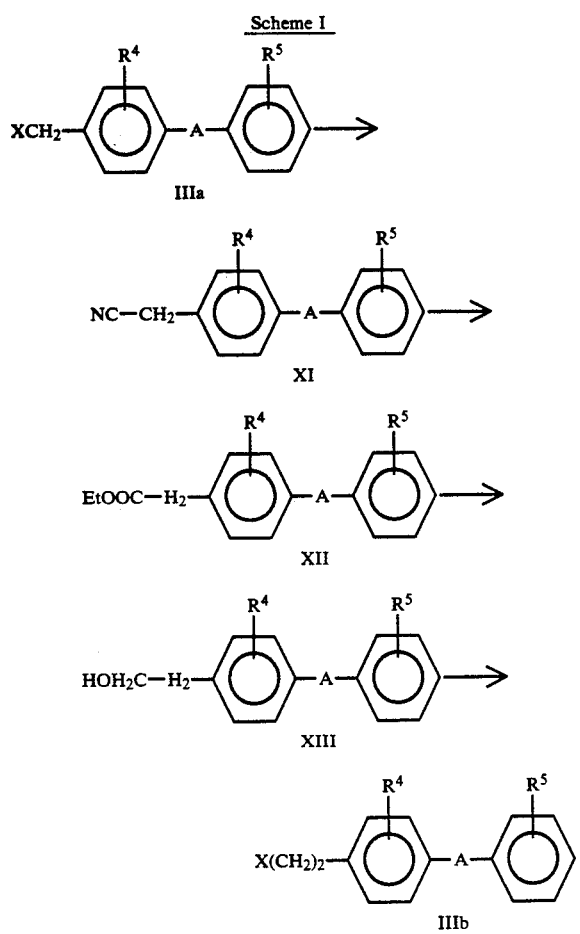

wherein each group has the above-defined meaning.

The compounds (I) and salts thereof according to the present invention strongly inhibit vasoconstriction and hypertension derived by angiotensin II and therefore possess potent anti-hypertensive activity in animals, more specifically mammal animals (e.g. humans, dogs, rabbits, rats, etc.). Further, the compounds (I) and salts thereof according to the present invention are of quite low toxicity and useful in treating not only hypertension but also circulatory system diseases such as heart diseases, strokes and the like.

For therapeutic use, the compounds (I) and salts thereof can be administered as pharmaceutical compositions (e.g., powders, granules, tablets, pills, capsules, injections, solutions and the like) comprising at least one such compound alone or in admixture with pharmaceutically acceptable carriers, excipients and/or diluents. The pharmaceutical compositions can be formulated in accordance with conventional methods.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. When used for treating adult essential hypertension, the active ingredient will preferably be administered in an appropriate amount, for example, selected from the range of about 10 mg to 100 mg a day orally and from the range of about 5 mg to 50 mg a day intravenously. The active ingredient will preferably be administered in equal doses two or three times a day.

The foregoing is merely illustrative of the invention and is not intended to limit the invention to the disclosed compounds. Variations and changes which are obvious to one skilled in the art are intended to be within the scope and nature of the invention.

EXAMPLE

The invention is further illustrated but in no way limited by the following reference examples, working examples, pharmaceutical examples and experimental examples.

In the specification of the present application, examples of the abbreviations used are given below. Me:-Methyl, Et:Ethyl, Pr:Propyl, Bu:Butyl, iBu:Isobutyl, tBu:Tert-butyl, Ph:Phenyl, DMF:Dimethylformamide.

REFERENCE EXAMPLE 1

Isobutyl 2-ethyl-4-hydroxythieno[2,3-b]pyridine-5-carboxylate

A mixture of 2-ethyl-4-hydroxythieno[2,3-b]pyridine-5-carboxylic acid (200 mg, 0.9 mmol) and boron trifluoride-ethyl ether (47%, 0.5 ml) in isobutyl alcohol (10 ml) was heated under reflux for 5 hours. The reaction mixture was allowed to cool and concentrated to dryness. The resulting residue was purified by flash column chromatography on silica gel. The column was eluted with chloroform/ethyl acetate (3:1) to give 80 mg (31%) of the title compound as colorless crystals.

mp. 156°–158° C.

IR (KBr)cm$^{-1}$: 1700, 1595, 1520.

NMR (CDCl$_3$)δ: 1.05(6H, d, J=6.6 Hz), 1.40(3H, t, J=7.4 Hz), 2.0–2.2(1H, m), 2.94(2H, q, J=7.4, 15.0 Hz), 4.20(2H, d, J=6.6 Hz), 7.16(1H, s), 8.84(1H, s).

| Elemental Analysis for C$_{14}$H$_{17}$NO$_3$.H$_2$O | | |
|---|---|---|
| C (%) | H (%) | N (%) |
| Calcd: C, 63 38; | H, 5.70; | N, 15.84 |
| Found: C, 63.70; | H, 5.44; | N, 15.50. |

REFERENCE EXAMPLE 2

2-Methoxyethyl 2-ethyl-4-hydroxythieno[2,3-b]pyridine-5-carboxylate

A mixture of 2-ethyl-4-hydroxythieno[2,3-b]pyridine-5-carboxylic acid (380 mg, 1.7 mmol) and DMF (0.13 ml, 1.7 mmol) in benzene (5 ml) was heated to 60° C. and to the reaction mixture was added thionyl chloride (0.15 ml, 2.1 mmol). The mixture was stirred at 60° C. for 3 hours and then allowed to cool with an ice bath. The precipitated product was collected by filtration and washed with benzene. The resulting precipitate (223 mg) was dissolved in a mixture of 2-methoxyethanol (0.3 ml) and CH$_2$Cl$_2$ (5 ml) and then triethyamine (0.7 ml) were added to the solution. The mixture was stirred for 30 minutes and poured into chloroform. The resulting mixture was washed with 1N hydrochloric acid, dried (MgSO$_4$) and evaporated in vacuo. The resulting residue was purified by flash column chromatography on silica gel. The column was eluted with ethyl acetate/hexane/chloroform (1:1:1) and then chloroform/methanol (9:1) to give 200 mg (41%) of the title compound as colorless powders.

IR (KBr)cm$^{-1}$: 1700, 1590, 1530, 1480.

NMR (CDCl$_3$)δ: 1.39(3H, t, J=7.4 Hz), 2.94(2H, q, J=7.4, 15.0 Hz), 3.45(3H, s), 3.7–3.8(2H, m), 4.5–4.6(2H, m), 7.17(1H, s), 8.87(1H, s).

|  | Elemental Analysis for C$_{13}$H$_{15}$NO$_4$S | | |
|---|---|---|---|
|  | C (%) | H (%) | N (%) |
| Calcd: | C, 55.50; | H, 5.37; | N, 4.98 |
| Found: | C, 55.47; | H, 5.38; | N, 4.95 |

REFERENCE EXAMPLE 3

Ethyl 2-ethyl-4-hydroxy-3-nitrothieno[2,3-b]pyridine-5-carboxylate

A solution of ethyl 2-ethyl-4-hydroxythieno[2,3-b]pyridine-5-carboxylate (1.0 g, 4.0 mmol) in conc. sulfuric acid (10 ml) was cooled to −5° C. and a solution of sodium nitrate (370 mg, 4.3 mmol) in conc. sulfuric acid (5 ml) was added dropwise to the chilled solution. The reaction mixture was stirred at −3° C. to −5° C. for 1 hour and poured into ice-water. The precipitated product was collected by filtration and washed with cold water and then ethanol. The resulting precipitate was dissolved in chloroform, washed with a saturated aqueous sodium chloride, dried (MgSO$_4$) and evaporated in vacuo. The resulting yellow solid was washed with a mixture of ether/hexane, and dried to give 960 mg (81%) of the title compound.

mp 194°–201° C. (dec.).

IR (KBr)cm$^{-1}$: 1700, 1600, 1590, 1530.

NMR (CDCl$_3$)δ: 1.42(3H, t, J=7.4 Hz), 1.47(3H, t, J=7.2 Hz), 3.05(2H, q, J=7.4, 15.0 Hz), 4.50(2H, q, J=7.2, 14.4 Hz), 8.93(1H, s).

|  | Elemental Analysis for C$_{12}$H$_{12}$N$_2$O$_5$S | | |
|---|---|---|---|
|  | C (%) | H (%) | N (%) |
| Calcd: | C, 48.64; | H, 4.08; | N, 9.45 |
| Found: | C, 48.48; | H, 4.01; | N, 9.28 |

REFERENCE EXAMPLE 4

Ethyl 2-ethyl-7-[[2'-(N-trityltetrazol-5-yl)biphenyl-4-yl]methyl]-4-oxo-4,7-dihydrothieno[2,3-b]pyridine-5-carboxylate To a solution of ethyl 2-ethyl-4-hydroxy-thieno[2,3-b]pyridine-5-carboxylate (1.00 g, 4 mmol) in 20 ml of DMF) was added sodium hydride (60% dispersion in oil, 160 mg) and the mixture was stirred for 10 minutes. To the reaction mixture was added 4-[2'-(N-trityltetrazol-5-yl)phenyl]benzyl bromide (2.23 g, 4 mmol) and the mixture was heated at 90° C. for 1 hour with stirring. The reaction mixture was poured into water followed by extraction with ethyl acetate. The organic layer was washed with water, dried (MgSO$_4$), and evaporated to dryness. The resulting residue was purified by flash column chromatography on silica gel. The column was eluted with ethyl acetate/dichloromethane (1:1) to give 2.24 g (77%) of the title compound as white crystals.

mp 195°–198° C.

IR (KBr)cm$^{-1}$: 1730, 1705, 1620.

NMR (CDCl$_3$)δ: 1.27(3H, t, J=9.6 Hz), 1.39(3H, t, J=6.8 Hz), 2.72(2H, q, J=8.9, 15.0 Hz), 4.38(2H, q, J=7.2, 13.8 Hz), 5.02(2H, s), 6.80–8.0(9H, m), 8.29(1H, s).

|  | Elemental Analysis for C$_{45}$H$_{37}$N$_5$O$_3$S | | |
|---|---|---|---|
|  | C (%) | H (%) | N (%) |
| Calcd: | C, 74.26; | H, 5.12; | N, 9.62 |
| Found: | C, 74.09; | H, 5.18; | N, 9.50 |

The following compounds (II) can be easily prepared by or according to the known techniques, for example, as disclosed in:

(1) P. Blaszkiewicz, H. Vorbruggen and H. J. Kesler (Schering AG): DOS 2, 447,477 (15. 4. 76); Chem. Abst., 85, 46627 (1976), (2) Y. Kuwada, K. Meguro, Y. Sato and T. Fugono (Takeda Chem.): DOS 2, 435,025 (6. 25. 75); Chem. Abst., 82, 156252 (1975), (3) R. K. Russell, J. B. Plress, R. A. Rampulla, J. J. McNally, R. Falotico, J. A. Keiser, D. A. Bright and A. Tobia, J. Med. Chem., 31, 1786 (1988), (4) M. Suwada, T. Sakamoto, K. Tabata, K. Endo, K. Ito, M. Kobayashi and H. Fuumi, Chem. Pharm. Bull., 37, 2091 (1989), (5) M. Sugiyama, T. Sakamoto, K. Tabata and H. Fuumi, Chem. Pharm. Bull., 37, 2717 (1989), (6) G. D. Madding and M. D. Thompson, J. Heterocyclic Chem., 24, 581 (1987), (7) J. Barker, P. R. Huddleston and D. Holmes, J. Chem. Research (S), 1985, 214, (8) J. Barker, P. R. Huddleston and D. Holmes, J. Chem. Research (S), 1986, 122, (9) M. A. Khan and A. E. Guarconi, J. Heterocyclic Chem., 14, 807 (1977),

(10) K. Ogawa, I. Yamawaki, Y. Matsusita, N. Nomura and I. Okazaki, WO 89/02432.

The compounds (III) can alternatively be prepared in the same manner as described in Reference Example 1, 2, or 3.

TABLE 1

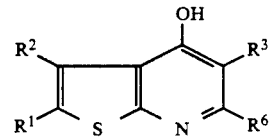

| Reference Example No. | R$^1$ | R$^2$ | R$^3$ | R$^6$ | mp (°C.) |
|---|---|---|---|---|---|
| 5-1 | Br | H | COOEt | H | 208–209 |
| 5-2 | H | H | COOEt | H | 105–108 |
| 6 | Me | H | COOEt | H | 122–124 |
| 7 | Pr | H | COOEt | H | 74–75 |
| 8 | Et | H | COOCH$_2$CH$_2$OMe | H | powder |
| 9 | Et | H | CH$_2$OH | H | >260 (decomp.) |

TABLE 2

(II)

[Structure: thieno-pyrimidinedione with R1, R2, R7 substituents]

| Reference Example No. | R1 | R2 | R7 | mp (°C.) |
|---|---|---|---|---|
| 10 | Et | H | Bu | 217–220 |
| 11 | Et | H | —CH2—C6H5 | 259–262 |
| 12 | Et | H | Et | 243–244 |
| 13 | Et | H | —C6H4—F (4-F-phenyl) | >290 |
| 14 | Et | H | 2,4-dichlorophenyl | 268–275 |
| 15 | Et | H | cyclohexyl | 285–288 |

TABLE 2-continued (II)

| Reference Example No. | R1 | R2 | R7 | mp (°C.) |
|---|---|---|---|---|
| 16 | Et | H | —CH2COOEt | 201–204 |
| 17 | Et | H | —CH2CH2N(piperazinyl)-(2-OMe-C6H4) | 239–241 |

The following compounds (Reference Examples 18–32) were prepared in the same manner as in Reference Example 4.

TABLE 3

[Structure with R2, R1, R3, R12 substituents; biphenyl-tetrazole moiety]

| Reference Example No. | R1 | R2 | R3 | R12 | Yield (%) | mp (°C.) |
|---|---|---|---|---|---|---|
| 18 | Et | H | —COOCH2CH2OCH3 | —C(Ph)3 | 30 | 192–198 |
| 19 | Et | H | —COOiBu | —C(Ph)3 | 40 | 209–212 |
| 20 | Et | NO2 | —COOEt | —C(Ph)3 | 34 | |
| 21 | Me | H | —COOEt | —C(Ph)3 | 53 | 205–207 |
| 22 | Pr | H | —COOEt | —C(Ph)3 | 51 | 181–187 |
| 23 | Br | H | —COOEt | —C(Ph)3 | 47 | 129–133 |
| 24 | H | H | —COOEt | —C(Ph)3 | 50 | 137–139 |
| 25 | Et | H | —CH2OH | —C(Ph)3 | 46 | powder |
| 26 | Et | H | H | —C(Ph)3 | 46 | |
| 27 | Et | H | —CHO | —C(Ph)3 | 67 | 150–156 |
| 28 | Et | H | —CH=CH—COOtBu | —C(Ph)3 | 56 | powder |
| 29 | Et | H | —COOEt | —COOtBu | 62 | |
| 30 | CN | H | —COOEt | —C(Ph)3 | 21 | 129–131 |
| 31 | Et | H | —CONCH2PH CH3 | —C(Ph)3 | 56 | 169–171 |
| 32 | Et | H | —CH2OMe | —C(Ph)3 | 26 | powder |

The following compounds (Reference Examples 33–40) were prepared in the same manner as in Reference Example 4.

TABLE 4a

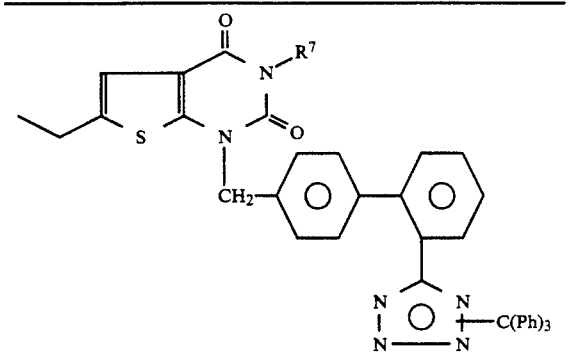

| Reference Example No. | R⁷ | mp (°C.) | Yield (%) |
|---|---|---|---|
| 33 | Bu | 173–176 | 57 |
| 34 | —CH₂—C₆H₅ | 204–207 | 47 |
| 35 | Et | 117–122 | 57 |
| 36 | —C₆H₄—F | 192–193 | 67 |
| 37 | —C₆H₃Cl₂ | 193–197 | 79 |
| 38 | —C₆H₁₁ (H) | 141–144 | 48 |
| 39 | —CH₂COOEt | 181–183 | 63 |
| 40 | —CH₂CH₂N(piperazinyl-(2-methoxyphenyl)) | powder | 93 |

TABLE 4b

| Reference Example No. | ¹H-NMR (200MH₂, CDCl₃) δ |
|---|---|
| 33 | 0.96(3H, t), 1.24(3H, t), 1.3–1.5(2H, m), 1.5–1.7(2H, m), 2.66(2H, q), 4.04(2H, t), 5.01(2H, s), 7.00(1H, s), 6.8–7.5(22H, m), 7.9–8.0(1H, m) |
| 34 | 1.22(3H, t), 2.65(2H, q), 5.00(2H, s), 5.23(2H, s), 7.00(1H, s), 6.8–8.0(28H, m) |
| 35 | 1.24(3H, t), 1.27(3H, t), 2.66(2H, q), 4.11(2H, q), 5.01(2H, s), 6.8–7.5(23H, m), 7.9–8.0(1H, m), |
| 36 | 1.28(3H, t), 2.72(2H, q), 5.03(2H, s), 6.8–8.0(28H, m) |
| 37 | 1.26(3H, t), 2.68(2H, q), 5.06(2H, q), 6.8–8.0(27H, m) |
| 38 | 1.23(3H, t), 1.2–2.6(10H, m), 2.65(2H, q), |

TABLE 4b-continued

| Reference Example No. | ¹H-NMR (200MH₂, CDCl₃) δ |
|---|---|
|  | 4.8–5.0(1H, m), 4.97(2H, s), 6.8–7.9(24H, m) |
| 39 | 1.23(3H, t), 1.29(3H, t), 2.65(2H, q), 4.24(2H, q), 4.79(2H, s), 5.02(2H, s), 6.8–8.0(24H, m) |
| 40 | 1.23(3H, t), 2.64(2H, q), 2.7–3.2(10H, m), 3.85(3H, s), 4.2–4.4(2H, m), 5.03(2H, s), 6.8–7.5(27H, m), 7.9–8.0(1H, m) |

WORKING EXAMPLE 1

A: Ethyl 2-ethyl-7-[2'-cyanobiphenyl-4-yl)methyl]-4-oxo-4,7-dihydrothieno[2,3-b]pyridine-5-carboxylate Ethyl 2-ethyl-4-hydroxythieno[2,3-b]-pyridine-5-carboxylate (250 mg, 1 mmol) and 4-(2'-cyanophenyl)benzyl chloride (250 mg, 1.1 mmol) were dissolved in 5 ml of N,N-dimethylformamide (DMF). To the solution was added potassium carbonate (150 mg) and the mixture was stirred at 90° C. for 2 hours. The reaction mixture was poured into water followed by extraction with ethyl acetate. The organic layer was washed with water, dried (MgSO₄), and evaporated to dryness. The resulting residue was purified by flash column chromatography on silica gel. The column was eluted with ethyl acetate/dichloromethane (1:1) to give 254 mg (60%) of the title compound as crystals.

NMR (CDCl₃)δ: 1.30(3H, t, J=6 Hz), 1.39(3H, t, J=6 Hz), 2.81(2H, q, J=6, 15 Hz), 4.40(2H, q, J=6, 13.5 Hz), 5.27(2H, s), 7.25–8.0(9H, m), 8.37(1H, s).

B: Ethyl 2-ethyl-7-[[2'-(1H-tetrazol-5-yl)biphenyl-4-yl]methyl]-4-oxo-4,7-dihydrothieno[2,3-b]pyridine-5-carboxylate and 2-ethyl-7-[[2'-(1H-tetrazol-5-yl)biphenyl-4-yl]methyl]-4-oxo-4,7-dihydrothieno[2,3-b]pyridine-5-carboxylic acid A solution of the compound (250 mg, 0.59 mmol) prepared in Working Example 1A, sodium azide (390 mg, 5.9 mmol) and ammonium chloride (300 mg, 5.9 mmol) in DMF (15 ml) was stirred at 110° C. for 10 days. After cooling, the reaction mixture was poured into water followed by extraction with ethyl acetate. The organic layer was washed with water, dried (MgSO₄), and evaporated to dryness. The resulting residue was purified by flash column chromatography on silica gel. The column was eluted with chloroform/methanol (9:1) to give 37 mg (13%) of ethyl 2-ethyl-7-[[2'-(1H-tetrazol-5-yl)biphenyl-4-yl]methyl]-4-oxo-4,7-dihydrothieno[2,3-b]pyridine-5-carboxylate as pale yellow powders.

IR (KBr)cm⁻¹: 1720, 1600, 1550, 1505.

NMR (CD₃OD)δ: 1.31(3H, t, J=7.6 Hz), 1.36(3H, t, J=7.0 Hz), 2.85(2H, q, J=7.6, 15.0 Hz), 4.33(2H, q, J=7.0, 14.2 Hz), 5.45(2H, s), 7.15(2H, d, J=8.6 Hz), 7.21(1H, s), 7.28(2H, d, J=8.6 Hz), 7.5–7.7(4H, m), 8.75(1H, s).

The column was further eluted with chloroform/methanol (9:1) to give 7 mg (2.7%) of 2-ethyl-7-[[2'-(1H-tetrazol-5-yl)biphenyl-4-yl]-methyl]-4-oxo-4,7-dihydrathieno[2,3-b]pyridine-5-carboxylic acid as white solids.

IR (KBr)cm⁻¹: 1650, 1605, 1580, 1540, 1505.

NMR (CD₃OD)δ: 1.34(3H, t, J=7.6 Hz), 2.89(2H, q, J=8.6, 15.0 Hz), 5.47(2H, s), 7.15(2H, d, J=8.2 Hz), 7.24(1H, s), 7.28(2H, d, J=8.2 Hz), 7.5–7.7(4H, m).

WORKING EXAMPLE 2

Ethyl 2-ethyl-7-[[2'-(1H-tetrazol-5-yl)biphenyl-4-yl]methyl]-4-oxo-4,7-dihydrothieno[2,3-b]pyridine-5-carboxylate A solution of the compound (727 mg, 1 mmol) prepared in Reference Example 4 in 20 ml of trifluoroacetic acid/water (1:3) was stirred at room temperature for 1 hour. The reaction mixture was poured into water followed by extraction with chloroform. The organic layer was washed with water, dried (MgSO$_4$), and evaporated to dryness. The resulting residue was purified by flash column chromatography on silica gel. The column was eluted with chloroform/methanol (9:1) to give 1.28 g (86%) of the title compound as colorless crystals. This product was identified by comparing with NMR and IR spectra of the compound obtained in Working Example 1B.

M.p. 161°–164° C.

| Elemental Analysis for $C_{26}H_{23}N_5O_3S\cdot H_2O$ | | | |
|---|---|---|---|
| | C (%) | H (%) | N (%) |
| Calcd: | C, 62.01; | H, 5.00; | N, 13.91 |
| Found: | C, 62.05; | H, 4.59; | N, 13.78 |

The following compounds as listed in Table 5 were prepared in the same manner as in Working Examples 2.

TABLE 5A

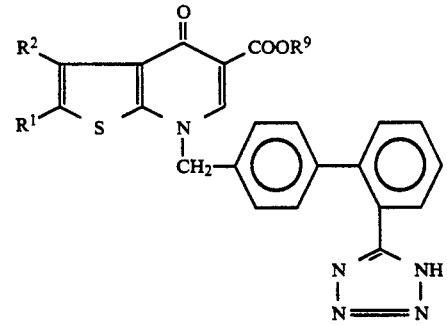

| Working Example No. | R$^1$ | R$^2$ | R$^9$ | mp (°C.) | IR(KBr) (cm$^{-1}$) |
|---|---|---|---|---|---|
| 3 | Br | H | Et | 254–260 (decomp.) | 1725, 1680, 1610, 1560, 1500 |
| 4 | H | H | Et | 245–249 | 1720, 1600, 1560 |
| 5 | Me | H | Et | 249–253 | 1710, 1675, 1605, 1560, 1505 |
| 6 | n-Pr | H | Et | 108–110 | 1720, 1605, 1550, 1505 |
| 7 | Et | H | i-Bu | 256–259 (decomp.) | 1720, 1670, 1605, 1560, 1500 |
| 8 | Et | H | CH$_2$CH$_2$OMe | 201–210 | 1720, 1680, 1605, 1560, 1505 |
| 9 | Et | NO$_2$ | Et | 214~ (decomp.) | 1720, 1700, 1615, 1550, 1510 |

TABLE 5b

| Working Example No. | NMR (DMSO-d$_6$) δ | E. Anal. (Calcd/Found) C (%), H (%), N (%) |
|---|---|---|
| 3 | 1.29(3H, t, J = 7.2Hz), 4.24(2H, q, J = 7.2, 14.2Hz), 5.46(2H, s), 7.13(2H, d, J = 8.2Hz), 7.29(2H, d, J = 8.2Hz), 7.5–7.7(5H, m), 8.79(1H, s) | C$_{24}$H$_{18}$BrN$_5$O$_3$S 53.74; 3.38; 13.06 53.57; 3.34; 12.80 |
| 4 | 1.29(3H, t, J = 7.2Hz), 4.24(2H, q, J = 7.2, 14.2Hz), 5.51(2H, s), 7.13(2H, d, J = 8.0Hz), 7.27(2H, d, J = 8.0Hz), 7.3–7.8(8H, m), 8.80(1H, s) | C$_{24}$H$_{19}$N$_5$O$_3$S .0.5H$_2$O 61.79; 4.32; 15.01 61.94; 4.17; 14.80 |
| 5 | 1.29(3H, t, J = 7.2Hz), 2.44(3H, d, J = 1.0Hz), 4.23(2H, q, J = 7.2, 14.2Hz), 5.45(2H, s),7.08(1H, d, J = 1.0Hz), 7.13(2H, d, J = 8.0Hz), 7.25(2H, d, J = 8.0Hz), 7.5–7.7(4H, m), 8.74(1H, s) | C$_{26}$H$_{21}$N$_5$O$_3$S 63.68; 4.49; 14.85 63.39; 4.47; 14.67 |
| 6 | 0.91(3H, t, J = 7.2Hz), 1.28(3H, t, J = 7.0Hz), 1.61(2H, q, J = 7.2,15.0Hz), 2.76(2H, t, J = 7.6Hz), 4.23(2H, q, J = 7.0, 14.2Hz), 5.45(2H, s), 7.10(1H, s)7.12(2H, d, J = 8.4Hz), 7.26(2H, d, J = 8.4Hz), 7.5–7.7(4H, m), 8.74(1H, s) | C$_{27}$H$_{25}$N$_5$O$_3$S .H$_2$O 62 65; 5.26; 13.53 62 55; 4.84; 13.38 |
| 7 | 0.96(6H, d, J = 6.8Hz), 1.23(3H, t, J = 7.4Hz), 1.9–2.1(1H, m), 2.80(2H, q, J = 7.4,15.0Hz), 3.97(2H, d, J = 6.6Hz), 5.46(2H, s), 7.11(1H, s), 7.13(2H, d, J = 8.0Hz), 7.27(2H, d, J = 8.0Hz), 7.5–7.7(4H, m), 8.70(1H, s) | C$_{28}$H$_{27}$N$_5$O$_3$S .0.5H$_2$O 64.35; 5.40; 13.40 64.22; 5.24; 13.47 |
| 8 | 1.23(3H, t, J = 7.4Hz), 2.81(2H, q, J = 7.4, 15.0Hz), 3.30(3H, s), 3.62 2H, t, J = 4.8Hz), 4.31(2H, t, J = 4.8Hz) 5.46(2H, s), 7.11(1H, s), 7.12(2H, d, J = 8.0Hz), 7.25(2H, d, J = 8.0Hz), 7.5–7.7(4H, m), 8.73(1H, s) | |
| 9 | 1.20(3H, t, J = 7.4Hz), 1.29(3H, t, J = 7.0Hz), 2.83(2H, q, J = 7.4, 15.4Hz), | C$_{26}$H$_{22}$N$_6$O$_5$S .H$_2$O 56.93; 4.41; 15.32 |

TABLE 5b-continued

| Working Example No. | NMR (DMSO-d$_6$) δ | E. Anal. (Calcd/Found) C (%), H (%), N (%) |
|---|---|---|
| | 4.24(2H, q, J = 7.0, 14.0Hz), 5.53(2H, s), 7.14(2H, d, J = 8.2Hz), 7.30(2H, d, J = 8.2Hz), 7.5–7.7(4H, m), 8.86(1H, s) | 57.12; 4.05; 15.26 |

WORKING EXAMPLE 10

2-Ethyl-7-[[2'-(1H-tetrazol-5-yl)biphenyl-4-yl]methyl]-4-oxo-4,7-dihydrothieno[2,3-b]pyridine-5-carboxylic acid Ethyl 2-ethyl-7-[[2'-(1H-tetrazol-5-yl) biphenyl-4-yl]methyl]-4-oxo-4,7-dihydrothieno[2,3-b]pyridine-5-carboxylate (600 mg, 1.235 mmol) was dissolved in 6 ml of 1N sodium hydroxide and the mixture was heated at 100° C. for 20 minutes with stirring. After cooling, 7 ml of 1N hydrochloric acid was added to the reaction mixture and the mixture was extracted with chloroform. The organic layer was washed with water, dried (MgSO$_4$), and evaporated to dryness. The resulting crystal was washed with dichloromethane and dried to give 550 mg of the title compound as colorless crystals. This product was identified by comparing with NMR and IR spectra of the compound obtained in Working Example 1B.

M.p. 153°–157° C.

| Elemental Analysis for C$_{24}$H$_{19}$N$_5$O$_3$.3.5H$_2$O | | | |
|---|---|---|---|
| | C (%) | H (%) | N (%) |
| Calcd: | C, 55.38; | H, 5.03; | N, 13.48 |
| Found: | C, 54.75; | H, 3.93; | N, 13.15 |

WORKING EXAMPLE 11

A: Ethyl 2-ethyl-7-[(2'-t-butoxycarbonylbiphenyl-4-yl)methyl]-4-oxo-4,7-dihydrothieno[2,3-b]pyridine-5-carboxylate A mixture of ethyl 2-ethyl-4-hydroxythieno[2,3-b]pyridine-5-carboxylate (200 mg, 0.8 mmol), 4-(2-t-butoxycarbonylphenyl)benzyl bromide (300 mg, 0.9 mmol) and cesium carbonate (650 mg, 2.0 mmol) in DMF (10 ml) was stirred at 60° C. for 3 hours and further at 100° C. for an additional hour. After cooling, the reaction mixture was poured into water followed by extraction with ethyl acetate. The organic layer was washed with water, dried (MgSO$_4$), and evaporated to dryness. The resulting residue was purified by flash column chromatography on silica gel to give 258 mg (62%) of the title compound as crystals.

IR (KBr)cm$^{-1}$: 1720, 1705, 1690, 1510.

NMR (CDCl$_3$)δ: 1.20(9H, s), 1.32(3H, t, J=7.6 Hz), 1.41(3H, t, J=7.2 Hz), 2.81(2H, q, J=7.6, 14.6 Hz), 4.40(2H, q, J=7.2, 14.2 Hz), 5.23(2H, s), 7.2–7.5(8H, m), 7.81(1H, dd, J=1.6, 7.6 Hz), 8.42(1H, s).

| Elemental Analysis for C$_{30}$H$_{31}$NO$_5$S | | | |
|---|---|---|---|
| | C (%) | H (%) | N (%) |
| Calcd: | C, 69.61; | H, 6.04; | N, 2.71 |
| Found: | C, 69.85; | H, 6.15; | N, 2.37 |

B: Ethyl 2-ethyl-7-[(2'-carboxybiphenyl-4-yl)methyl]-4-oxo-4,7-dihydrathieno[2,3-b]pyridine-5-carboxylate To 5 ml of trifluoroacetic acid under ice-cooling were added the compound (200 mg, 0.39 mmol) prepared in Working Example 11A and anisole (0.1 ml) and the mixture was stirred for 2.5 hours. The reaction mixture was concentrated to dryness in vacuo. To the resulting residue was added dichloromethane followed by evaporation to dryness in vacuo. These treatments were repeated twice and ether was added to the resulting residue to precipitate solids which were filtered and dried to give 167 mg (93%) of the title compound as pale yellow powders.

IR (KBr)cm$^{-1}$: 1715, 1680, 1605.

NMR (d$_6$-DMSO) δ: 1.23(3H, t, J=7.4 Hz), 1.29(3H, t, J=7.2 Hz), 2.80(2H, q, J=7.4, 15.0 Hz), 4.23(2H, q, J=7.2, 13.8 Hz), 5.49(2H, s), 7.11(1H, s), 7.3–7.6(7H, m), 7.73(1H, d, J=7.4 Hz), 8.77(1H, s).

| Elemental Analysis for C$_{26}$H$_{23}$NO$_5$S.0.3H$_2$O | | | |
|---|---|---|---|
| | C (%) | H (%) | N (%) |
| Calcd: | C, 66.88; | H, 5.09; | N, 3.00 |
| Found: | C, 67.03; | H, 5.14; | N, 2.95 |

WORKING EXAMPLE 12

2-Ethyl-5-(N-benzylcarbamoyl)-7-[[2'-(1H-tetrazol-5-yl)biphenyl-4-yl]methyl]-thieno[2,3-b]pyridin-4(7H)-one A mixture of the compound (123 mg, 0.25 mmol) prepared in Working Example 2 and benzylamine (2 ml) was stirred at 60° C. for 3 days. After cooling, the reaction mixture was poured into chloroform, washed twice with 1N hydrochloric acid, dried (MgSO$_4$), and concentrated. The resulting residue was purified by flash column chromatography on silica gel. The column was eluted with chloroform/methanol (19:1 to 9:1) to give 63 mg (45%) of the title compound as crystals.

mp 177°–180° C.

IR (KBr)cm$^{-1}$: 1650, 1590, 1550, 1500.

NMR (DMSO-d$_6$)δ: 1.25(3H, t, J=7.4 Hz), 2.83(2H, q, J=7.4 Hz, 14.2 Hz), 4.56(2H, d, J=5.8 Hz), 5.57(2H, s), 7.0–7.7(14H, m), 8.95(1H, s).

| Elemental Analysis for C$_{31}$H$_{26}$N$_6$O$_2$S | | | |
|---|---|---|---|
| | C (%) | H (%) | N (%) |
| Calcd: | C, 68.11; | H, 4.79; | N, 15.37 |
| Found: | C, 68.06; | H, 4.79; | N, 15.17 |

The following compounds as listed in Table 6 were prepared in the same manner as in Working Examples 12.

TABLE 6a

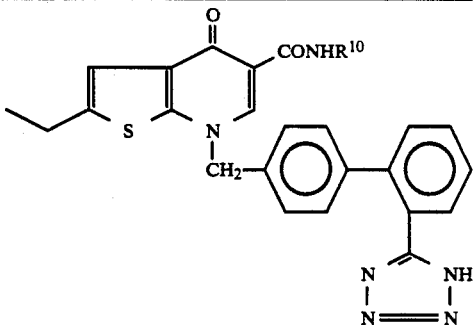

| Working Example No. | R[10] | mp (°C.) | IR(KBr) (cm$^{-1}$) |
|---|---|---|---|
| 13 | H | 267–270 | 1635, 1575, 1540, 1500 |
| 14 | CH$_2$CH(Me)$_2$ | 248–251 (decomp.) | 1655, 1590, 1555, 1525, 1510 |
| 15 | CH$_2$CH$_2$OH | 155–159 | 1655, 1595, 1550, 1520 |
| 16 | C$_6$H$_5$ | 215–218 | 1655, 1595, 1545, 1505 |

TABLE 6b

| Working Example No. | NMR (DMSO-d$_6$) δ | E. Anal. (Calcd/Found) C (%), H (%), N (%) |
|---|---|---|
| 13 | 1.25(3H, t, J = 7.6Hz), 2.83(2H, q, J = 7.6, 14.8Hz), 5.54(2H, s), 7.12(2H, d, J = 8.2Hz), 7.22(1H, s), 7.26(2H, d, J = 8.2Hz), 7.5–7.7(4H, m), 8.91(1H, s), 9.46(1H, bs) | C$_{24}$H$_{20}$N$_6$O$_2$S . H$_2$O<br>60.75; 4.67; 17.71<br>61.09; 4.41; 17.37 |
| 14 | 0.93(6H,d, J = 6.6Hz), 1.25(3H, t, J = 7.4Hz), 1.7–1.9(1H, m), 2.84(2H, d, J = 7.4, 14.0Hz), 3.18(2H, t, J = 6.2Hz), 5.55(2H, s), 7.11(2H, d, J = 8.2Hz), 7.19(1H, s), 7.25(2H, d, J = 8.2Hz), 7.5–7.7(4H, m), 8.90(1H, s) | C$_{28}$H$_{28}$N$_6$O$_2$S . H$_2$O<br>63.38; 5.70; 15.84<br>63.70; 5.44; 15.50 |
| 15 | 1.25(3H, t, J = 7.4Hz), 2.84(2H, q, J = 7.4, 16.0Hz), 3.3–3.6(4H, m), 4.81(1H, bs), 5.55(2H, s), 7.11(2H, d, J = 8.2Hz), 7.18(1H, s), 7.24(2H, d J = 8.2Hz), 7.5–7.7(4H, m), 8.31(1H, s), 8.90(1H, s) | |
| 16 | 1.27(3H, t, J = 7.4Hz), 2.87(2H, q, J = 7.4, 14.6Hz), 5.59(2H, s), 7.0–7.8 (14H, m), 9.05(1H, s) | C$_{30}$H$_{24}$N$_6$O$_2$S . 0.5H$_2$O<br>66.53; 4.65; 15.52<br>66.28; 4.51; 15.26 |

WORKING EXAMPLE 17

Ethyl 3-acetylamino-2-ethyl-7-[[2'-(1H-tetrazol-5-yl)biphenyl-4-yl]methyl]-4-oxo-4,7-dihydrothieno[2,3-b]pyridine-5-carboxylate Ethyl 2-ethyl-3-nitro-7-[[2'-(N-trityltetrazol-5-yl)biphenyl-4-yl)methyl]-4-oxo-4,7-dihydrothieno[2,3-b]pyridine-5-carboxylate (200 mg, 0.26 mmol) was dissolved in a mixture of acetic anhydride (6 ml), acetic acid (6 ml), dioxane (4 ml) and tetrahydrofuran (5 ml) and the solution was heated to 70° C. To the heated solution were added zinc powders (85 mg) and the reaction mixture was stirred for 2 hours. The insoluble material was removed from the reaction mixture by filtration and the filtrate was concentrated to dryness in vacuo. The resulting oil was dissolved in a mixture of trifluoroacetic acid (8 ml) and water (1 ml) and the solution was stirred at room temperature for 5 hours. The reaction mixture was poured into water and extracted with chloroform. The organic layer was washed with water, dried (MgSO$_4$), and evaporated to dryness. The resulting residue was purified by flash column chromatography on silica gel. The column was eluted with chloroform/methanol (20:1) to give 59 mg (42%) of the title compound as white crystals. mp 163°–166° C.

IR (KBr)cm$^{-1}$: 1720, 1700, 1615, 1550, 1510.

NMR (CDCl$_3$)δ: 1.14(3H, t, J=7.4 Hz), 1.29(3H, t, J=7.0 Hz), 2.03(3H, s), 2.63(2H, q, J=7.4, 15.0 Hz), 4.23(2H, q, J=7.0, 14.2 Hz), 5.45(2H, s), 7.13(2H, d, J=8.2 Hz), 7.28(2H, d, J=8.2 Hz), 7.5–7.7(4H, m), 8.74(1H, s), 9.66(1H, Bs).

| Elemental Analysis for C$_{28}$H$_{26}$N$_6$O$_4$S.H$_2$O | | | |
|---|---|---|---|
| | C (%) | H (%) | N (%) |
| Calcd: | C, 59.99; | H, 5.03; | N, 14.99 |
| Found: | C, 59.50; | H, 4.56; | N, 14.76 |

The following compounds (Working Examples 18–20) as listed in Table 7 were prepared in the same manner as in Working Examples 12.

TABLE 7a

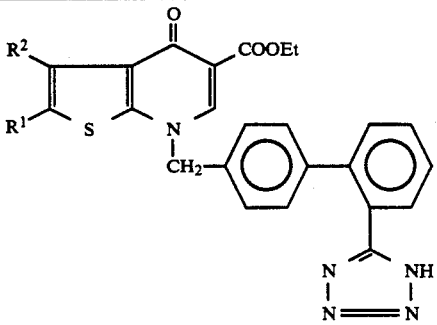

| Working Example No. | R$^1$ | R$^2$ | mp (°C.) | Yield (%) |
|---|---|---|---|---|
| 18 | H | Me | 167–170 | 30 |
| 19 | Br | Me | 227–231 | 77 |
| 20 | CN | H | 250–256 | 20 |

TABLE 7b

| Working Example No. | NMR (DMSO-d$_6$) δ | E. Anal. (Calcd/Found) C (%), H (%) N (%) |
|---|---|---|
| 18 | 1.28(3H, t), 2.47(3H, s), 4.22(2H, q), 5.44(2H, s), 6.92(1H, s), 7.10(2H, d), 7.23(2H, d), 7.5–7.7(4H, m), 8.70(1H, s) | C$_{25}$N$_{21}$N$_5$O$_3$S. 0.2H$_2$O 63.20; 4.54; 14.74 63.00; 4.37; 14.80 |
| 19 | 1.29(3H, t), 2.45(3H, s), 4.23(2H, q), 5.43(2H, s), 7.13(1H, d), 7.27(2H, d), 7.5–7.8(4H, m), 8.73(1H, s) | C$_{25}$H$_{20}$BrN$_5$O$_3$S 54.55; 3.66; 12.72 54.82; 3.63; 12.83 |
| 20 | 1.29(3H, t), 4.25(2H, q), 5.52(2H, s), 7.13(2H, d), 7.31(2H, d), 7.5–7.8 (4H, m), 8.25(1H, s), 8.89(1H, s) | |

The following compounds (Working Examples 21–36) were prepared in the same manner as in Working Example 12.

TABLE 8a

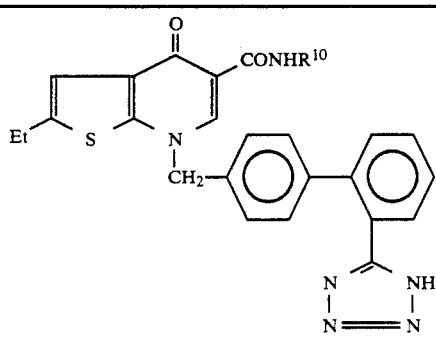

| Working Example No. | R$^{10}$ | mp (°C.) | Yield (%) |
|---|---|---|---|
| 21 | —CH$_2$—C$_6$H$_4$—OMe (2-OMe) | 134–148 | 42 |
| 22 | —CH$_2$—C$_6$H$_4$—OMe (4-OMe) | 223–225 | 67 |
| 23 | —CH$_2$—C$_6$H$_4$—F (4-F) | 202–204 | 54 |
| 24 | —CH$_2$—C$_6$H$_4$—F (3-F) | powder | 72 |
| 25 | —CH(CH$_3$)—C$_6$H$_5$ | 154–157 | 55 |
| 26 | —CH$_2$—C$_6$H$_4$—F (2-F) | 146–149 | 33 |

TABLE 8a-continued
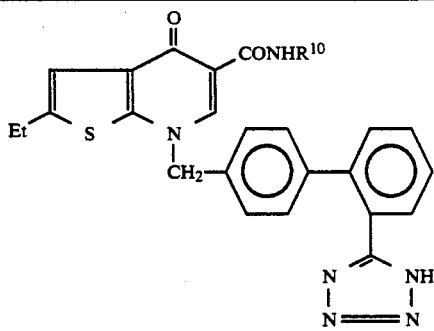
| Working Example No. | R[10] | mp (°C.) | Yield (%) |
|---|---|---|---|
| 27 | 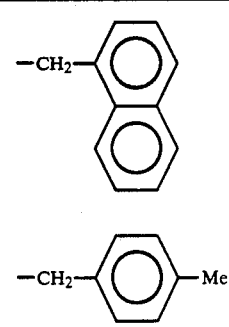 | 170-173 | 45 |
| 28 | 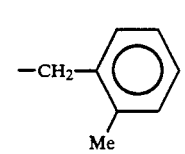 | 207-209 | 62 |
| 29 | 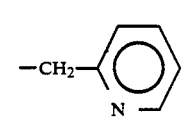 | 150-154 | 57 |
| 30 | 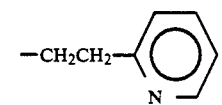 | 223-226 | 38 |
| 31 | 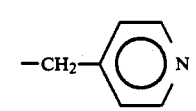 | 266-269 | 28 |
| 32 | 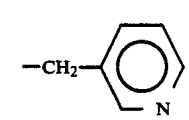 | 205-209 | 30 |
| 33 | 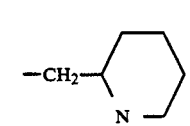 | 244-248 | 63 |
| 34 | 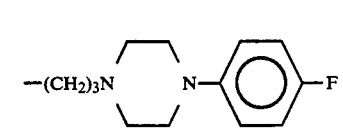 | powder | 72 |
| 35 | —(CH$_2$)$_3$N〈piperazinyl〉—⟨C$_6$H$_4$⟩—F | 247-248 | 33 |

TABLE 8a-continued

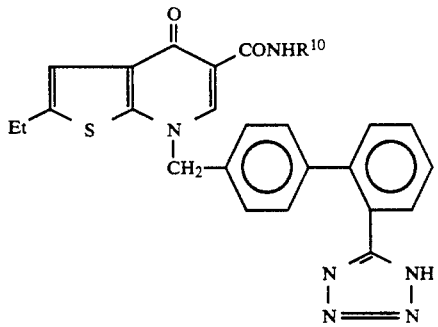

| Working Example No. | $R^{10}$ | mp (°C.) | Yield (%) |
|---|---|---|---|
| 36 | —(CH$_2$)$_4$N⟨N—⟨C$_6$H$_4$⟩—F | 188–190 | 36 |

TABLE 8b

| Working Example No | NMR (200MHz, CDCl$_3$) δ | E. Anal. (Calcd/Found) C (%), H (%), N (%) |
|---|---|---|
| 21 | 1.36(3H, t), 2.89(2H, q), 3.88(3H,s), 4.61(2H, d), 5.12(2H, s), 6.8–7.6 (12H, m), 8.05–8.15(1H, m), 8.30(1H, s) | |
| 22 | 1.37(3H, t), 2.89(2H, q), 3.78(3H, s), 4.57(2H, s), 5.20(2H, s), 7.6–8.0 (13H, m), 8.39(1H, s) | C$_{32}$H$_{28}$N$_6$O$_3$S .H$_2$O 64.63; 5.08; 14.13 64.92; 4.74; 13.99 |
| 23 | 1.38(3H, t), 2.91(2H, q), 4.60(2H, d), 5.18(2H, s), 6.9–7.6(12H, m), 8.1–8.2 (1H, m), 8.29(1H, s), 10.99(1H, brs) | C$_{31}$H$_{25}$FN$_6$O$_2$S 65.94; 4.46; 14.88 65.94; 4.45; 14.71 |
| 24 | 1.37(3H, t), 2.90(2H, q), 4.61(2H, d), 5.16(2H, s), 6.8–7.6(12H, m), 8.05–8.15(1H, m), 8.34(1H, s) | |
| 25 | 1.38(3H, t), 1.58(3H, d), 2.91(2H, q), 5.13(2H, s), 5.22(1H, t), 7.1–7.6 (13H, m), 8.1–8.2(1H, m), 8.20(1H, s), 11.05(1H, bs) | C$_{32}$H$_{28}$N$_6$O$_2$S .0.5H$_2$O 67.47; 5.13; 14.75 67.64; 4.99; 14.52 |
| 26 | 1.37(3H, t), 2.90(2H, q), 4.67(2H, d), 5.16(2H, s), 7.0–7.6(12H, m), 8.05–8.15(1H, m), 8.29(1H, s), 10.97 (1H, brs) | C$_{31}$H$_{25}$FN$_6$O$_2$S. 1.5H$_2$O 62.93; 4.77; 14.20 63.02; 4.30; 14.03 |
| 27 | 1.35(3H, t), 2.86(2H, q), 5.07(2H, s), 5.10(2H, s), 7.1–7.9(14H, m), 8.07 (2H, d), 8.31(1H, brs), 11.01(1H, brs); (CDCl$_3$) | C$_{35}$H$_{28}$N$_6$O$_2$S .0.5H$_2$O 69.40; 4.83; 13.87 69.40; 4.65; 13.64 |
| 28 | 1.37(3H, t), 2.31(3H, s), 2.90(2H, q), 4.57(2H, d), 5.15(2H, s), 7.0–7.6 (12H, m), 8.0–8.2(1H, m), 8.27(1H, brs); (CDCl$_3$) | C$_{32}$H$_{28}$N$_6$O$_2$S .0.5H$_2$O 67.47; 5.13; 14.75 67.54; 5.14; 14.57 |
| 29 | 1.37(3H, t), 2.38(3H, s), 2.90(2H, q), 4.61(2H, d), 5.16(2H, s), 7.0–7.6 (12H, m), 8.0–8.2(1H, m), 8.25(1H, brs;) (CDCl$_3$) | C$_{32}$H$_{28}$N$_6$O$_2$S .0.2H$_2$O 68.11; 5.07; 14.89 68.01; 4.85; 14.94 |
| 30 | 1.32(3H, t), 2.83(3H, q), 4.65(2H, d), 5.35(2H, s), 7.0–8.1(13H, m), 9.34(1H, s), 11.05(1H, t); (CDCl$_3$) | C$_{30}$H$_{25}$N$_7$O$_2$S .HCl 0.5H$_2$O 60.75; 4.59; 16.53 60.83; 4.29; 16.36 |
| 31 | 1.24(3H, t), 2.85(2H, q), 3.01(2H, t), 3.6–3.8(2H, m), 5.54(2H, s), 7.0–7.8 (12H, m), 8.5–8.6(1H, m), 8.88(1H, s), 10.20(1H, t); (DMSO-d$_6$) | C$_{31}$H$_{27}$N$_7$O$_2$S .0.5H$_2$O 65.25; 4.95; 17.18 65.27,4.79; 17.13 |
| 32 | 1.38(3H, t), 2.91(2H, q), 4.90(2H, s), 5.34(2H, s), 7.20(2H, d), 7.28(2H, d), 7.37(1H, s), 7.5–7.8(4H, m), 7.96(2H, d), 8.62(1H, s), 8.78(2H, d); (CDCl$_3$) | SIMS; 548(MH$^+$) |
| 33 | 1.25(3H, t), 2.85(2H, q), 4.73(2H, d), 5.57(2H, s), 7.12(2H, d), 7.20(1H, s), 7.26(2H, d), 7.5–8.9(8H, m), 8.93(1H, s), 10.71(1H, t); (DMSO-d$_6$) | C$_{30}$H$_{25}$N$_7$O$_2$S .HCl. 0.5H$_2$O 58.11; 4.88; 15.81 57.86; 4.34; 15.60 |
| 34 | 1.26(3H, t), 1.3–1.9(6H, m), 2.86(2H, q), 3.0–3.7(5H, m), 5.57(2H, s), 7.14 (2H, d), 7.21(1H, s), 7.23(2H, d), | SIMS; 554(MH$^{+1}$) |

TABLE 8b-continued

| Working Example No | NMR (200MHz, CDCl₃) δ | E. Anal. (Calcd/Found) C (%), H (%), N (%) |
|---|---|---|
| | 7.4–7.7(4H, m), 8.6(1H, brs), 8.91(1H, s), 10.40(1H, t); (DMSO-d₆) | |
| 35 | 1.28(3H, t), 1.78–1.94(2H, m), 2.56–2.94(6H, m), 3.09–3.27(4H, m), 3.39–3.76(2H, m), 5.53(2H, s), 6.93–7.32 (6H, m), 7.43–7.66(4H, m), 8.90(1H, s); (DMSO-d₆) | C₃₇H₃₇FN₈O₂S. 0.5H₂O 64.76; 5.58; 16.34 64.74; 5.84; 16.12 |
| 36 | 1.19(3H, t), 1.25(3H, t), 1.74–1.96 (2H, m), 2.66–3.56(16H, m), 5.55(2H, s), 6.90–7.31(9H, m), 7.43–7.72(4H, m), 8.92(1H, s); DMSO-d₆) | C₃₈H₃₉FN₈O₂S. 3.5H₂O 60.54; 6.15; 14.86 60.31; 5.96; 14.85 |

The following compounds (Working Examples 37–45) were prepared in the same manner as in Working Example 12.

TABLE 9a

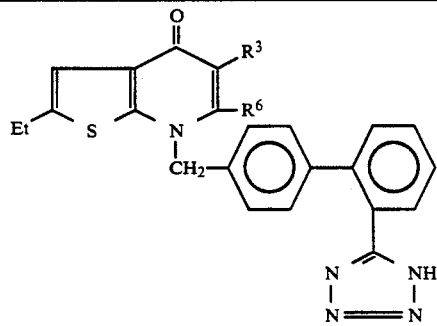

| Working Example No. | R³ | R⁶ | mp (°C.) | Yield (%) |
|---|---|---|---|---|
| 37 | —CH₂OH | H | >260 (dec.) | 73 |
| 38 | H | H | 249–253 | 83 |
| 39 | —CHO | H | powder | 66 |
| 40 | —CH=CHCOOtBu | H | powder | 100 |
| 41 | —CON(CH₃)—CH₂—C₆H₅ | H | >190 (dec.) | 88 |
| 42 | —CH₂OMe | H | 213–216 | 82 |
| 43 | —COOH | CH₃ | 162–167 | |
| 44 | —CONH—C₆H₅ | CH₃ | 175–180 | |
| 45 | —COOMe | —CH₂COOMe | | |

TABLE 9b

| Working Example No. | NMR (200MHz) δ | E. Anal. (Calcd/Found) C (%), H (%), N (%) |
|---|---|---|
| 37 | 1.24(3H, t), 2.79(2H, q), 4.40(2H, s), 7.05(1H,s), 7.11(2H, d), 7.22(2H, d), 7.5–7.8(4H, m), 7.98(1H, s); (DMSO-d₆) | C₂₄H₂₁N₅O₂S. 0.8H₂O 62.95; 4.97; 15.29 63.18; 4.88; 14.86 |
| 38 | 1.24(3H, t), 2.80(2H, q), 5.35(2H, s), 6.21(1H, d), 7.07(1H, s), 7.11(2H, d), 7.24(2H, d), 7.4–7.8(4H, m), 8.08(1H, d); (DMSO-d₆) | C₂₃H₁₉N₅OS. H₂O 64.02; 4.91; 16.23 63.87; 4.44; 15.90 |
| 39 | 1.24(3H, t), 2.82(2H, q), 5.50(2H, s), 7.12(2H, d), 7.20(1H, s), 7.28(2H, d), 7.5–7.7(4H, m), 8.69(1H, s), 10.28(1H, | |

TABLE 9b-continued

| Working Example No. | NMR (200MHz) δ | E. Anal. (Calcd/Found) C (%), H (%), N (%) |
|---|---|---|
| | s); (DMSO-$d_6$) | |
| 40 | 1.25(3H, t), 1.37(9H, s), 2.80(2H, q), 5.35(2H, s), 6.93(1H, d), 7.1-7.9(10H, m), 8.55(1H, s); (DMSO-$d_6$) | |
| 41 | 1.19(3H, t), 1.21(3H, t), 2.69(2H, q), 2.96(3H, s), 4.58(2H, s), 4.79(2H, s), 5.38(2H, s), 6.7-7.6(13H, m), 7.9-8.0 (1H, m), 8.6(1H, brs); (CDCl$_3$) | $C_{32}H_{28}N_6O_2S \cdot 0.5H_2O$ 67.47; 5.13; 14.75 67.64; 4.99; 14.52 |
| 42 | 1.21(3H, t), 2.69(2H, q), 3.44(3H, s), 4.09(2H, s), 5.21(2H, s), 6.8-7.9(10H, m); (CDCl$_3$) | $C_{25}H_{23}N_5O_2S \cdot 0.5H_2O$ 63.87; 5.23; 14.90 64.00; 4.99; 14.69 |
| 43 | 1.27(3H, t), 2.88(2H, q), 2.95(3H, s), 5.68(2H, s), 7.11(4H, s), 7.29(1H, s), 7.5-7.8(4H, m); (DMSO-$d_6$) | $C_{25}H_{21}N_5O_3S \cdot 0.5H_2O$ 62.49; 4.61; 14.57 62.28; 4.36; 14.39 |
| 44 | 1.39(3H, t), 2.75(3H, s), 2.99(2H, q), 5.85(2H, s), 7.1-7.8(14H, m); (CD$_3$OD) | SIMS; 547(MH$^+$) |
| 45 | 1.32(3H, t), 2.86(2H, q), 3.66(3H, s), 3.88(3H, s), 3.94(2H, s), 5.55(2H, s), 6.98(2H, d), 7.13(2H, d), 7.22(1H, s) 7.4-7.7(4H, m); (CD$_3$OD) | SIMS; 544(MH$^+$) |

The following compounds (Working Examples 46–53) were prepared in the same manner as in Working Example 2.

TABLE 10a

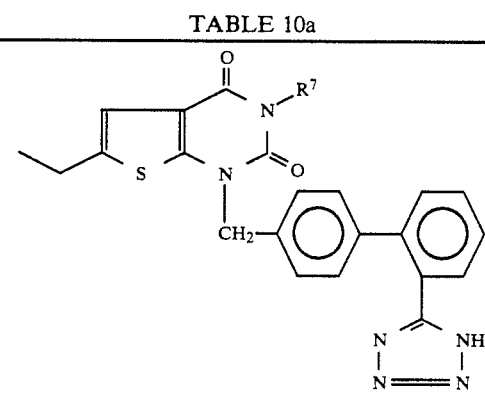

| Working Example No. | $R^7$ | mp (°C.) | Yield (%) |
|---|---|---|---|
| 46 | Bu | 127–130 | 32 |
| 47 | —CH$_2$—C$_6$H$_5$ | 202–205 | 65 |
| 48 | Et | 210–212 | 59 |
| 49 | —C$_6$H$_4$—F | 246–250 | 70 |

TABLE 10a-continued

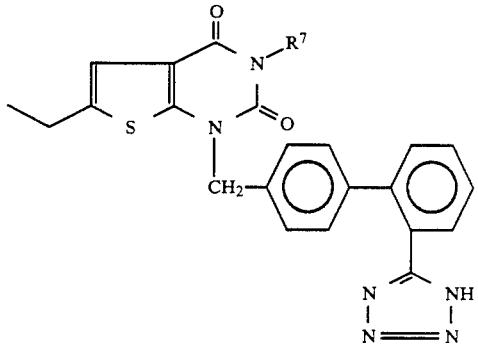

| Working Example No. | $R^7$ | mp (°C.) | Yield (%) |
|---|---|---|---|
| 50 | 2,4-dichlorophenyl | powder | 31 |
| 51 | cyclohexyl | 207–221 | 57 |
| 52 | —CH$_2$COOEt | 167–169 | 44 |
| 53 | —CH$_2$CH$_2$N(piperazinyl)-2-OMe-C$_6$H$_4$ | powder | 77 |

TABLE 10b

| Working Example No. | $^1$H-NMR (CDCl$_3$) δ | E. Anal. (Calcd/Found) C (%), H (%), N (%) |
|---|---|---|
| 46 | 0.92(3H, t), 1.30(3H, t), 1.2-1.5(2H, | $C_{26}H_{26}N_6O_2S$ |

TABLE 10b-continued

| Working Example No. | $^1$H-NMR (CDCl$_3$) δ | E. Anal. (Calcd/Found) C (%), H (%), N (%) |
|---|---|---|
| | m), 1.5–1.8(2H, m), 2.77(2H, q), 4.01 (2N, t), 5.15(2H, s), 7.00(1H, s), 7.23(2H, d), 7.42(2H, d), 7.5–7.7(3H, m), 8.1–8.2(1H, m) | 64.18; 5.39; 17.27 64.00; 5.51; 17.18 |
| 47 | 1.21(3H, t), 2.75(2H, q), 5.12(2H, s), 5.15(2H, s), 7.02(1H, s), 7.09(2H, d), 7.2–7.8(11H, m) | C$_{29}$H$_{24}$N$_6$O$_2$S .0.4H$_2$O 65.99; 4.74; 15.92 66.17; 4.91; 15.63 |
| 48 | 1.25(3H, t), 1.30(3H, t), 2.78(2H, q), 4.08(2H, q), 5.16(2H, s), 7.01(1H, s), 7.23(2H, d), 7.43(2H, d), 7.5–7.7(3H, m), 8.1–8.2(1H, m) | C$_{24}$H$_{22}$N$_6$O$_2$S .0.5H$_2$O 61.65; 4.96; 17.97 61.70; 4.83; 17.80 |
| 49 | 1.32(3H, t), 2.81(2H, q), 5.14(2H, s), 7.06(1H, s), 7.1–7.8(12H, m) | C$_{28}$H$_{21}$FN$_6$O$_2$S 64.11; 4.04; 16.02 63.82; 3.97; 15.77 |
| 50 | 1.33(3H, t), 2.81(2H, q), 5.20(2H, q), 7.07(1H, s), 7.2–8.2(11H, m) | C$_{28}$H$_{20}$N$_6$O$_2$SCl$_2$. 0.6H$_2$O 57.36; 3.64; 14.33 57.74; 3.75; 13.75 |
| 51 | 1.29(3H, t), 1.2–2.6(10H, m), 2.76 (2H, q), 4.7–5.0(1H, m), 5.13(2H, s), 6.99(1H, s), 7.24(2H, d), 7.42(2H, d), 7.5–7.7(3H, m), 8.1–8.2(1H, m) | C$_{28}$H$_{28}$N$_6$O$_2$S. 0.4H$_2$O 64.69; 5.58; 16.17 64.81; 5.50; 15.95 |
| 52 | 1.29(3H, t), 1.31(3H, t), 2.79(2H, q), 4.23(2H, q), 4.80(2H, s), 5.17(2H, s), 7.03(1H, s), 7.22(2H, d), 7.4–7.7(5H, m), 8.1–8.2(1H, m) | C$_{26}$H$_{24}$N$_6$O$_4$S 60.45; 4.68; 16.27 60.33; 4.59; 16.17 |
| 53 | 1.36(3H, t), 2.84(2H, q), 2.8–3.6(8H, m), 3.83(3H, s), 4.2–4.5(4H, m), 4.97 (2H, s), 6.8–7.2(7H, m), 7.4–7.6(5H, m), 7.94(1H, d) | C$_{35}$H$_{36}$N$_8$O$_3$S. CF$_3$COOH .2.5H$_2$O 55.01; 5.24; 13.87 54.51; 4.74; 13.45 |

PHARMACEUTICAL EXAMPLES

The compounds (I) of the present invention are employed, for example, when used as agents for treating circulatory system diseases such as hypertension, heart diseases, strokes and the like, in the following formulations.

1. Capsule

| | | |
|---|---|---|
| (1) | Ethyl 2-ethyl-7-[[2'-(1H-tetrazol-5-yl)biphenyl-4-yl]methyl]-oxo-4,7-dihydrothieno [2,3-b]pyridine-5-carboxylate | 10 mg |
| (2) | Lactose | 90 mg |
| (3) | Microcrystalline cellulose | 70 mg |
| (4) | Magnesium stearate | 10 mg |
| | One capsule | 180 mg |

The ingredients (1), (2), and (3) and a half of the ingredient (4) were blended together and granulated. To this mixture was added the remaining half of the ingredient (4) and distributed into gelatine capsules.

2. Tablet

| | | |
|---|---|---|
| (1) | Ethyl 2-ethyl-7[[2'-(1H-tetrazol-5-yl)biphenyl-4-yl]methyl]-4-oxo-4,7-dihydrathieno [2,3-b]pyridine-5-carboxylate | 10 mg |
| (2) | Lactose | 35 mg |
| (3) | Maize starch | 150 mg |
| (4) | Microcrystalline cellulose | 30 mg |
| (5) | Magnesium stearate | 5 mg |
| | One tablet | 230 mg |

Two third each of the ingredients (1), (2), (3) and (4) and a half of the ingredient (5) were blended together and granulated. To these granules were added the remaining ingredients (4) and (5) and then compressed to form tablets.

3. Injection

| | | |
|---|---|---|
| (1) | 2-Ethyl-7-[[2'-(1H-tetrazol-5-yl)biphenyl-4-yl]methyl]-4-oxo-4,7-dihydrothieno ]2,3-b]pyridine-5-carboxylic acid.sodium salt | 10 mg |
| (2) | Inositol | 100 mg |
| (3) | Benzyl alcohol | 20 mg |
| | One ampule | 130 mg |

The ingredients (1), (2) and (3) were dissolved in distilled water for injection to a total volume of two ml and distributed into ampules. Total processes were carried out under sterile conditions.

EXPERIMENTAL EXAMPLE 1

Inhibition of binding of angiotensin-II to angiotensin receptor

Method

An experiment of inhibition on the binding of angiotensin-II (A-II) to A-II-receptor was conducted by modifying the method of Douglas et al. [Endocrinology, 102, 685–696 (1978)]. An A-II-receptor was prepared from the membrane fraction of bovine adrenal cortex.

The compound of the present invention ($10^{-9}$M to $3 \times 10^{-5}$M) and $^{125}$I-A-II (1.85 kBq/50 μl) were added to the receptor membrane fraction, and the mixture was incubated at room temperature for one hour. The receptor-bound and free $^{125}$I-A-II were separated through a filter (Whitman GF/B filter), and the radioacitivity of $^{125}$I-A-II bound to the receptor was measured.

Results

The results relating to the compounds of the present invention are shown in Table 11.

EXPERIMENTAL EXAMPLE 2

Inhibitory effect of the compound of the present invention on pressor action of A-II

Method

Jcl: SD rats (9 week old, male) were used. On the day previous to the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A-II (100 ng/kg) as the control was measured. The drugs were orally administered, and then, at each point of the measurement, A-II was administered intravenously, and the pressor action was similarly measured. By comparing the pressor action before and after administration of the drug, the percent inhibition by the drug on A-II-induced pressor action was evaluated.

Results

The results relating to the compounds of the present invention are shown in Table 11.

TABLE 11

| Working Example No. | Radio Receptor Assay (% Inhibition) | | | Pressor Response (30 mg/Kg, p.o.) |
|---|---|---|---|---|
| | $10^{-7}$(M) | $10^{-6}$(M) | IC$_{50}$(M) | |
| 2 | 69 | 94 | 0.05 | NT |
| 3 | 51 | 81 | 0.07 | NT |
| 4 | 34 | 68 | 0.20 | NT |
| 5 | 56 | 88 | 0.05 | NT |
| 6 | 48 | 83 | 0.09 | NT |
| 7 | 40 | 82 | 0.17 | NT |
| 8 | 81 | 94 | 0.01 | NT |
| 10 | 51 | 86 | 0.04 | +*b |
| 11 | 42 | 83 | 0.21 | NT |
| 12 | 57 | 89 | 0.06 | ++ |
| 13 | 78 | 93 | 0.02 | NT |
| 14 | 45 | 87 | 0.13 | NT |
| 15 | 62 | 90 | 0.05 | NT |
| 16 | 47 | 85 | 0.12 | ++ |
| 20 | 22 | 56 | 0.67 | NT |
| 21 | 36 | 71 | 0.25 | ++ |
| 23 | 40 | 81 | 0.17 | ++ |
| 24 | 37 | 82 | 0.19 | ++ |
| 25 | 8 | 55 | 0.78 | ++ |
| 26 | 35 | 81 | 0.21 | ++ |
| 28 | 36 | 78 | 0.22 | + |
| 29 | 47 | 86 | 0.12 | ++ |
| 30 | 70 | 93 | 0.02 | ++ |

*a: NT, not tested.
*b: (% Inhibition), ++ ≧ 70% > + ≧ 50%.

It is understood that the preceding representative examples may be varied within the scope of the present invention by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A compound of the formula (Ia):

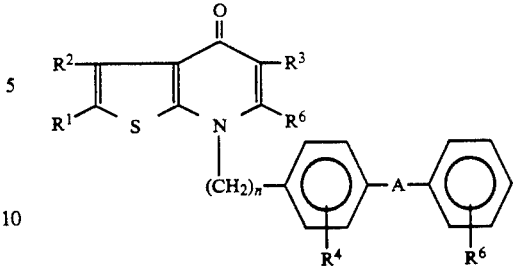

wherein $R^1$ and $R^2$ which may be the same or different, are each independently hydrogen, halogen, cyano, nitro, a group having the formula: $R^8CONH-$ wherein $R^8$ is hydrogen, lower alkyl of 1 to 8 carbon atoms, lower alkenyl of 2 to 8 carbon atoms, lower alkynyl of 2 to 8 carbon atoms, cycloalkyl of 3 to 8 carbon atoms, or an aromatic hydrocarbon having 6 to 12 carbon atoms, which may be substituted with hydroxyl, lower ($C_{1-4}$) alkoxy, lower ($C_{1-4}$) alkyl, halogen, nitro, amino, methyl amino, dimethylamino, phenylamino, benzylamino, morpholino, piperidino, piperazino, N-phenylpiperazino, acyloxy, optionally substituted phenyl, or a group having the formula: $-COD'$ wherein $D'$ is hydroxy, lower ($C_{1-4}$) alkoxy, amino, methyl amino, dimethylamino, phenylamino, benzylamino, morpholino, piperidino, piperazino, or N-phenylpiperazino, or a hydrocarbon residue selected from the group consisting of lower alkyl of 1 to 8 carbon atoms, lower alkenyl of 2 to 8 carbon atoms, lower alkynyl of 2 to 8 carbon atoms, cycloalkyl of 3 to 8 carbon atoms, and an aromatic hydrocarbon having 6 to 12 carbon atoms, which may be substituted with hydroxyl, lower ($C_{1-4}$) alkoxy, lower ($C_{1-4}$) alkyl, halogen, nitro amino, methyl amino, dimethylamino, phenylamino, benzylamino, morpholino, piperidino, piperazino, N-phenylpiperazino, acyloxy, optionally substituted phenyl, or a group having the formula: $-COD'$ wherein $D'$ is hydroxy, lower ($C_{1-4}$) alkoxy, amino, methyl amino, dimethylamino, phenylamino, benzylamino, morpholino, piperidino, piperazino, or N-phenylpiperazino;

$R^3$ is hydrogen, lower alkyl of 1 to 8 carbon atoms or lower alkenyl of 2 to 8 carbon atoms which may be straight or branched and may be optionally substituted with hydroxyl, amino, N-lower ($C_{1-4}$) alkyl amino, N,N-dilower ($C_{1-4}$) alkyl amino, halogen, lower ($C_{1-4}$) alkoxy, or $-COD''$ wherein $D''$ is lower ($C_{1-4}$) alkoxy, hydroxy, halogen, amino, N-lower ($C_{1-4}$) alkyl amino, N,N-dilower ($C_{1-4}$) alkyl amino, phenylamino, benzylamino, napthylmethylamino, morpholino, piperidino, piperazino, or N-phenylpiperazino, or $-COD$ wherein $D$ is hydrogen, lower ($C_{1-4}$) alkoxy, hydroxy, halogen, amino, N-lower ($C_{1-4}$) alkyl amino, N,N-dilower ($C_{1-4}$) alkyl amino, phenylamino, benzylamino, napthylmethylamino, morpholino, piperidino, piperazino, piperidylmethyl, N-(p-fluorophenyl)piperazino, or N-phenylpiperazino;

$R^4$ is hydrogen, halogen or nitro;

$R^5$ is carboxyl, lower ($C_{1-4}$) alkoxycarbonyl, cyano, tetrazolyl, trifluoromethanesulfonic amide, phosphoric acid, or sulfonic acid;

$R^6$ is hydrogen, lower alkyl of 1 to 8 carbon atoms or lower alkenyl of 2 to 8 carbon atoms which may be straight or branched and may be optionally substituted with hydroxyl, amino, N-lower ($C_{1-4}$) alkyl amino, N,N-dilower ($C_{1-4}$) alkyl amino, halogen, lower ($C_{1-4}$) alkoxy, or —COD" wherein D" is lower ($C_{1-4}$) alkoxy, hydroxy, halogen, N-lower ($C_{1-4}$) alkyl amino, N,N-dilower ($C_{1-4}$) alkyl amino, phenylamino, napthylamino, benzylamino, napthylmethylamino, morpholino, piperidino, piperazino, or N-phenylpiperazino;

A is a direct bond, lower ($C_{1-4}$) alkylene, —C(=O)—, —O—, —S—, —NH—, —C(=O)—NH—, —O—CH$_2$—, —S—CH$_2$—, or —CH=CH—; and n is an integer of 1 or 2;

or a pharmaceutically acceptable salt thereof.

2. A compound according to claim 1, wherein said acyloxy is lower ($C_{1-4}$) alkanoyloxy or benzoyloxy.

3. A compound according to claim 1, wherein said phenyl may be optionally substituted with halogen, nitro, lower ($C_{1-4}$) alkoxy, or lower ($C_{1-4}$) alkyl.

4. A compound according to claim 1, wherein said D is amino, methylamino, dimethylamino, phenylamino, benzylamino, morpholino, piperidino, piperazino, or N-phenylpiperazino.

5. A compound according to claim 1, wherein said $R^5$ is tetrazolyl.

6. A compound according to claim 1, wherein said $R^5$ is in the ortho position.

7. A compound according to claim 1, wherein said A is lower ($C_{1-4}$) alkylene, —C(=O)—, —O—, —S—, —NH—, —C(=O)—NH—, —O—CH$_2$—, —S—CH$_2$—, or —CH=CH—.

8. A compound according to claim 1, which is a compound of the formula (Ia'):

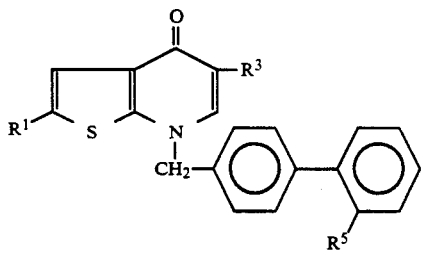

(Ia')

wherein $R^1$ is lower ($C_{1-8}$) alkyl; $R^3$ is lower ($C_{1-8}$) alkyl which may be optionally substituted with hydroxyl, amino, methylamino, dimethylamino, halogen, lower ($C_{1-4}$) alkoxy, or —COD" wherein D" is lower ($C_{1-4}$) alkoxy, hydroxy, halogen, amino, methylamino, dimethylamino, phenylamino, benzylamino, morpholino, piperidino, piperazino, N-phenylpiperazino, or COD wherein D is hydrogen, lower ($C_{1-4}$) alkoxy, hydroxy, halogen, amino, methylamino, dimethylamino, phenylamino, benzylamino, morpholino, piperidino, piperazino, or N-phenylpiperazino; and $R^5$ is carboxyl or tetrazolyl;

or a pharmaceutically acceptable salt thereof.

9. A compound according to claim 1 or a pharmaceutically acceptable salt thereof, which is selected from the group consisting of ethyl 2-ethyl-7-[[2'-(1H-tetrazol-5-yl)biphenyl-4-yl[methyl[-4-oxothieno[2,3-b]pyridine-5-carboxylate, 2-ethyl-7-[[2'-(1H-tetrazol-5-yl)biphenyl-4-yl]methyl]-4-oxothieno[2,3-b]pyridine-5-carboxylic acid, methoxyethyl 2-ethyl-7-[[2'-(1H-tetrazol-5-yl)biphenyl-4-yl]methyl]-4-oxothieno[2,3 -b]pyridine-5-carboxylate, 2-ethyl-5-(N-benzylcarbamoyl)-7-[[2'-(1H-tetrazol-5-yl)biphenyl-4-yl]methyl]-4-oxothieno[2,3-b]pyridine, 2-ethyl-5-(N-phenylcarbamoyl)-7-[[2'-(1H-tetrazol-5-yl)biphenyl-4-yl]methyl]-4-oxothieno[2,3-b]pyridine, and 2-ethyl-5-(N-2-pyridylmethylcarbamoyl)-7-[[2'-(1H-tetrazol-5-yl)biphenyl-4-yl]methyl]-4-oxo-thieno[2,3-b]pyridine.

10. A pharmaceutical composition for antagonizing angiotensin II which comprises a therapeutically effective amount of a compound according to claim 1 or a pharmaceutically acceptable salt thereof in admixture with a pharmaceutical acceptable carrier, excipient or diluent.

11. A method for antagonizing angiotensin II in a mammal which comprises administering a therapeutically effective amount of a compound according to claim 1 or a pharmaceutically acceptable salt thereof.

12. A method for antagonizing angiotensin II in a mammal which comprises administering a therapeutically effective amount of a compound according to claim 8 or a pharmaceutically acceptable salt thereof.

13. A pharmaceutical composition according to claim 10 which is in the form of a tablet.

* * * * *